(12) United States Patent
Zoldan et al.

(10) Patent No.: US 12,068,073 B1
(45) Date of Patent: Aug. 20, 2024

(54) SYSTEMS AND METHODS FOR CREDENTIALING AND PRIVILEGING OF HEALTHCARE PRACTITIONERS

(71) Applicant: HealthStream, Inc., Nashville, TN (US)

(72) Inventors: Scott Zoldan, Chicago, IL (US); Vicki Searcy, Lisbon (PT); Brandi Zevenbergen, Sioux City, IA (US)

(73) Assignee: HEALTHSTREAM, INC., Nashville, TN (US)

( * ) Notice: Subject to any disclaimer, the term of this patent is extended or adjusted under 35 U.S.C. 154(b) by 0 days.

(21) Appl. No.: 18/379,578

(22) Filed: Oct. 12, 2023

(51) Int. Cl.
*G16H 50/30* (2018.01)
*G06Q 30/018* (2023.01)
*G16H 10/60* (2018.01)
*G16H 40/20* (2018.01)

(52) U.S. Cl.
CPC .......... *G16H 40/20* (2018.01); *G06Q 30/018* (2013.01)

(58) Field of Classification Search
CPC .............................. G16H 40/20; G06Q 30/018
See application file for complete search history.

(56) References Cited

U.S. PATENT DOCUMENTS

| 2015/0242862 | A1* | 8/2015 | Rupple | G06Q 30/018 705/317 |
| 2021/0026980 | A1* | 1/2021 | Candelario | G06F 21/64 |
| 2023/0170079 | A1* | 6/2023 | Gnanasambandam | G16H 50/70 705/2 |

OTHER PUBLICATIONS

"Introducing CredentialStream", VerityStream, https://web.archive.org/web/20200811231253/https://www.veritystream.com/solution/credentialstream, Retrieved Aug. 11, 2020, in 8 pgs.

* cited by examiner

Primary Examiner — Maroun P Kanaan
(74) Attorney, Agent, or Firm — Andre J. Bahou; Lucas R. Yordy; Bradley Arant Boult Cummings LLP

(57) ABSTRACT

Systems and methods for credentialing and privileging are disclosed. The system may include at least one processor and at least one memory storing one or more non-transitory computer-executable instructions. The at least one processor may implement a method including the step of receiving from a healthcare practitioner a form request to receive a dynamic privilege form in one or more privilege categories for one or more facilities. The method may include generating a dynamic privilege form including one or more healthcare privileges and one or more facilities for selection by the healthcare practitioner based on the form request. The method may include sending the dynamic privilege form to the healthcare practitioner. The method may include receiving from the healthcare practitioner the dynamic privilege form including requested healthcare privileges from the one or more healthcare privileges and requested facilities from the one or more facilities.

29 Claims, 14 Drawing Sheets

FIG. 5B

SYSTEMS AND METHODS FOR CREDENTIALING AND PRIVILEGING OF HEALTHCARE PRACTITIONERS

TECHNICAL FIELD

The present disclosure generally relates to healthcare, and more particularly, to systems and methods for credentialing and privileging of healthcare practitioners.

BACKGROUND

Certain personnel that work at healthcare facilities are required to be credential and privileged in order to provide patient care services. Credentialing is the process of obtaining, verifying, and evaluating the qualifications of a healthcare practitioner who seeks to provide patient care services. Privileging is the process whereby the specific scope and content of patient care services (i.e., clinical privileges) are authorized for a health care practitioner by the healthcare organization based on evaluation of the individual's credentials and performance.

Clinical privileging & credentialing in healthcare organizations is a safeguard to protect patients by ensuring qualified and high-quality healthcare practitioners are delivering care to patients. It is the responsibility of the healthcare organizations governing board, usually through the medical staff bylaws and other applicable policies and procedures, to continuous enhance and improve the quality of care, including patient safety, effectiveness, efficiency, and equity of care for all patients admitted to or treated in the healthcare organization.

Current systems and procedures that healthcare organizations use to credential and privilege healthcare practitioners require users, reviewers, and decision makers to access numerous different data sources, forms, and systems to verify the credentials of practitioners, the privileges being sought, the conditions for maintaining those privileges, and verifying that such conditions have been met. These systems and procedures are susceptible to errors due to their distributed nature. Such errors can allow healthcare practitioners to perform patient health care services that they are not qualified or privileged to perform or to not be privileged to perform health care services that they are qualified to perform. These issues, in turn, can lead malpractice, harm to patients, and the associated legal risk.

Thus, what is needed are systems and methods that allow healthcare organizations to credential and privilege healthcare practitioners accurately and efficiently in the full scope of health care privileges for which the healthcare practitioners are qualified to perform.

BRIEF SUMMARY

This Brief Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one aspect, the present disclosure contemplates a system for credentialing and privileging of a healthcare practitioner. In one embodiment, the system may include at least one processor and at least one memory storing one or more non-transitory computer-executable instructions. The at least one processor may, in response to executing the one or more non-transitory computer-executable instructions, implement a method. The method may include the step of receiving a form request from a healthcare practitioner, wherein the form request includes a request to receive a dynamic privilege form in one or more privilege categories for one or more facilities. The method may also include the step of generating the dynamic privilege form based on the form request, the dynamic privilege form including one or more healthcare privileges and one or more facilities for selection by the healthcare practitioner and a plurality of prompts for the credentials of the healthcare practitioner. The method may include the step of sending a credential form including a plurality of prompts for the credentials of the healthcare practitioner. The method may also include the step of sending the dynamic privilege form to the healthcare practitioner. The method may include the step of receiving from the healthcare practitioner the credential form including one or more credential responses to the plurality of prompts. The method may also include the step of receiving from the healthcare practitioner the dynamic privilege form including requested healthcare privileges from the one or more healthcare privileges and requested facilities from the one or more facilities, and one or more credential responses.

In another embodiment, the system for credentialing and privileging of a healthcare practitioner may include at least one processor and at least one memory storing one or more non-transitory computer-executable instructions healthcare privilege data including required qualifications for the healthcare practitioner to perform one or more healthcare privileges at one or more facilities. The at least one processor may, in response to executing the one or more non-transitory computer-executable instructions, implement a method. The method may include the step of receiving from the healthcare practitioner a form request to receive a privilege form in one or more privilege categories for one or more facilities. The method may also include the step of sending to the healthcare practitioner a credential form including a plurality of prompts for the credentials of the healthcare practitioner. The method may further include the step of sending a privilege form from the plurality of privilege forms to the healthcare practitioner based on the form request. The privilege form may include the one or more healthcare privileges and the one or more facilities for selection by the healthcare practitioner. The method may include the step of receiving from the healthcare practitioner the credential form including one or more credential responses. The method may also include the step of receiving from the healthcare practitioner the privilege form including requested healthcare privileges from the one or more healthcare privileges and the requested facilities from the one or more facilities.

In another aspect, the present disclosure contemplates a system for analyzing outcomes of healthcare practitioner credentialing and privileging. The system may include at least one processor and at least one memory. The memory may store healthcare privilege data including required qualifications for healthcare practitioners to perform a plurality of healthcare privileges at a plurality of facilities; practitioner data including education data, certification data, and training data for a plurality of healthcare practitioners and current privilege data on the privileges granted to the plurality of healthcare practitioners privileged at the plurality of facilities; clinical activity data including volume data, type data, and outcome data of healthcare services provided by the plurality of healthcare practitioners; and one or more non-transitory computer-executable instructions. The at least one processor may, in response to executing the one or more non-transitory computer-executable instructions, implement a method. The method may include analyzing the healthcare privilege data, the practitioner privilege data, and the clinical activity data. The method may also include generating a recommendation to modify the required qualifications for one or more of the plurality of facilities based on the analyzing of the healthcare privilege data, the health care practitioner privilege data, the practitioner privilege data, and the clinical activity data.

The present disclosure includes several benefits that overcome the problems of the prior art. For example, prior art systems and methods for credentialing and privileging of healthcare providers require access to numerous information sources in order to cross reference the privileges requested at various facilities by a healthcare practitioner, the required qualifications for being granted the requested privileges at the requested facilities, and the qualifications of the healthcare practitioner. The systems and methods of the present disclosure may be used to centralize and provide access to such information into a single secure portal. The systems and methods of the present disclosure may provide automated review of privilege request forms and may route the privilege request, along with all associated data and prior information, to these reviewers based on their defined sequence/role through an integrated secure portal that facilitates collaboration and documents binding decisions.

The systems and methods of the present disclosure also facilitate the review of credentialing and privileging within a healthcare organization by comparing the results of healthcare credentialing and privileging across healthcare organizations. The systems and methods of the present disclosure may generate recommendations for changes to the qualifications required to be granted healthcare procedures at various facilities to improve the outcomes of healthcare procedures and improve patient safety. The systems and methods of the present disclosure may also generate recommendations for improving the credentialing and privileging process itself.

The systems and methods disclosed herein also improve the functioning of computers. For example, the systems and methods disclosed allow computers to generate dynamic privilege forms based on privilege request from healthcare practitioners seeking to be granting healthcare privileges at one or more facilities. The systems and methods disclosed herein provide automated review of privilege forms completed by healthcare practitioners for compliance with laws and regulations as well as compliance with all required credentials. The systems and methods disclosed also allow computers to identify and assign reviewers and administrators to a privilege request and facilitates the review process based on the role of such reviewers and administrators in the healthcare process.

It is understood that both the foregoing general description and the following detailed description are exemplary and exemplary only, and are not restrictive of the disclosure as claimed.

BRIEF DESCRIPTION OF THE DRAWINGS

The accompanying drawings, which are incorporated in and constitute a part of the specification, illustrate exemplary embodiments of the disclosure. Together with the description, they serve to explain the objects, advantages, and principles of the disclosure. In the drawings:

FIG. 5B is a front view illustrating another exemplary web portal displaying one embodiment of a privilege form for credentialing and privileging of healthcare practitioners displayed.

DETAILED DESCRIPTION

Overview

Reference will now be made in detail to exemplary embodiments of the disclosure, some aspects of which are illustrated in the accompanying drawings.

The present disclosure is directed to systems and methods for credentialing and privileging of healthcare practitioners. As discussed below, the systems and methods of the present disclosure may provide a system with the capability to receive requests from a user for privileges at one or more facilities. The system may request and verify the credentials of the user. The systems and methods may facilitate review of the healthcare provider's privilege request by the healthcare organization. In some embodiments, a user of the systems and methods disclosed herein may include a healthcare worker, a reviewer working on behalf of a healthcare organization, an administrator at a healthcare facility, or another type of user.

The present disclosure is also directed to systems and methods that, in some embodiments, provide functionality to ensure that the user requesting privileges at one or more facilities has the credentials and meets all conditions necessary to be granted the request privileges. The systems and methods may notify the user or a healthcare organization if the user does or does not have the credentials or meet the conditions. The present disclosure is also directed to systems and methods disclosed herein that may analyze and recommend that privileges be granted or denied to a user, that user request particular privileges, that the credentials or conditions for a privilege be changed, or make other recommendations throughout the credentialing and privileging process.

Figure 1:
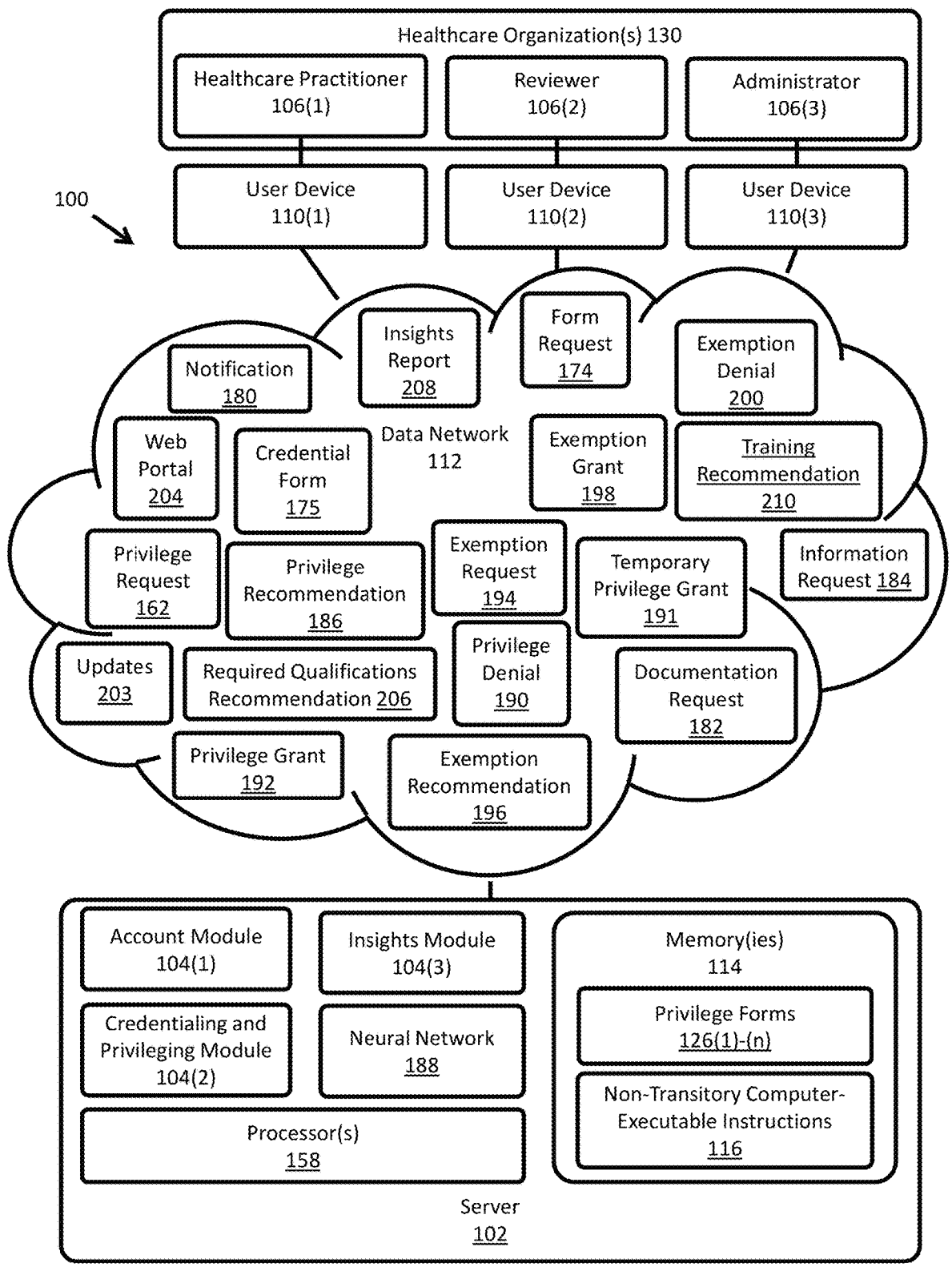
FIG. 1 is a schematic block diagram illustrating an exemplary system for credentialing and privileging of healthcare practitioners.

The following is a brief overview of one embodiment of a system 100 of the present disclosure. FIG. 1 depicts one embodiment of the system 100. The system 100 may include a server 102. The server 102 may include one or more modules 104(1)-(3). As discussed herein, a single module, in general, is referred to as a "module 104," a particular module is referred to as "module 104(1)," "module 104(2)," etc., and all of the one or more module are referred to as "modules 104(1)-(3)." Similar numbering practices may be used for other components in which more than one of such component may be used.

The modules 104(1)-(3) may carry out functionality of the server 102. In one embodiment, the server 102 may include an account module 104(1). The account module 104(1) may store data associated with one or more users 106(1)-(n) of the server 102 or one or more users 106(1)-(n) of the modules 104(1)-(3) of the server 102. The server 102 may include a credentialing and privileging module 104(2). The credentialing and privileging module 104(2) may facilitate the credentialing and privileging of a healthcare practitioner 106(1). The server 102 may include an insights module 104(3). The insights module 104(3) may analyze data and make recommendations for improving the credentialing and privileging process.

In one embodiment, the system 100 may include one or more user devices 110(1)-(n). Although three user devices 110(1)-(3) are depicted in FIG. 1, the system 100 may include any number of user devices 110(1)-(n). The one or more user devices 110(1)-(n) may communicate with the server 102 via a data network 112 of the system 100.

The following describes further details of one or more embodiments of the present disclosure. In some embodiments, the system 100 may include the server 102. The server 102 may include one or more computing devices, such as application servers, database servers, other types of servers, desktop computers, laptop computers, tablet computers, mobile computing devices, or other types of electronic devices. A computing device may include one or more processors, memory, one or more input/output (I/O) interfaces, or other computer components. The server 102 may include one or more modules 104(1)-(3). As used herein, the term "module" may refer to a software implementation, hardware implementation, or a combination of both. The module 104(1)-(3) may include functionality that carries out steps, instructions, operations, or the like. The modules 104(1)-(3) may be implemented using program instructions, circuitry, or other implementation methods, as are described herein.

Figure 2:
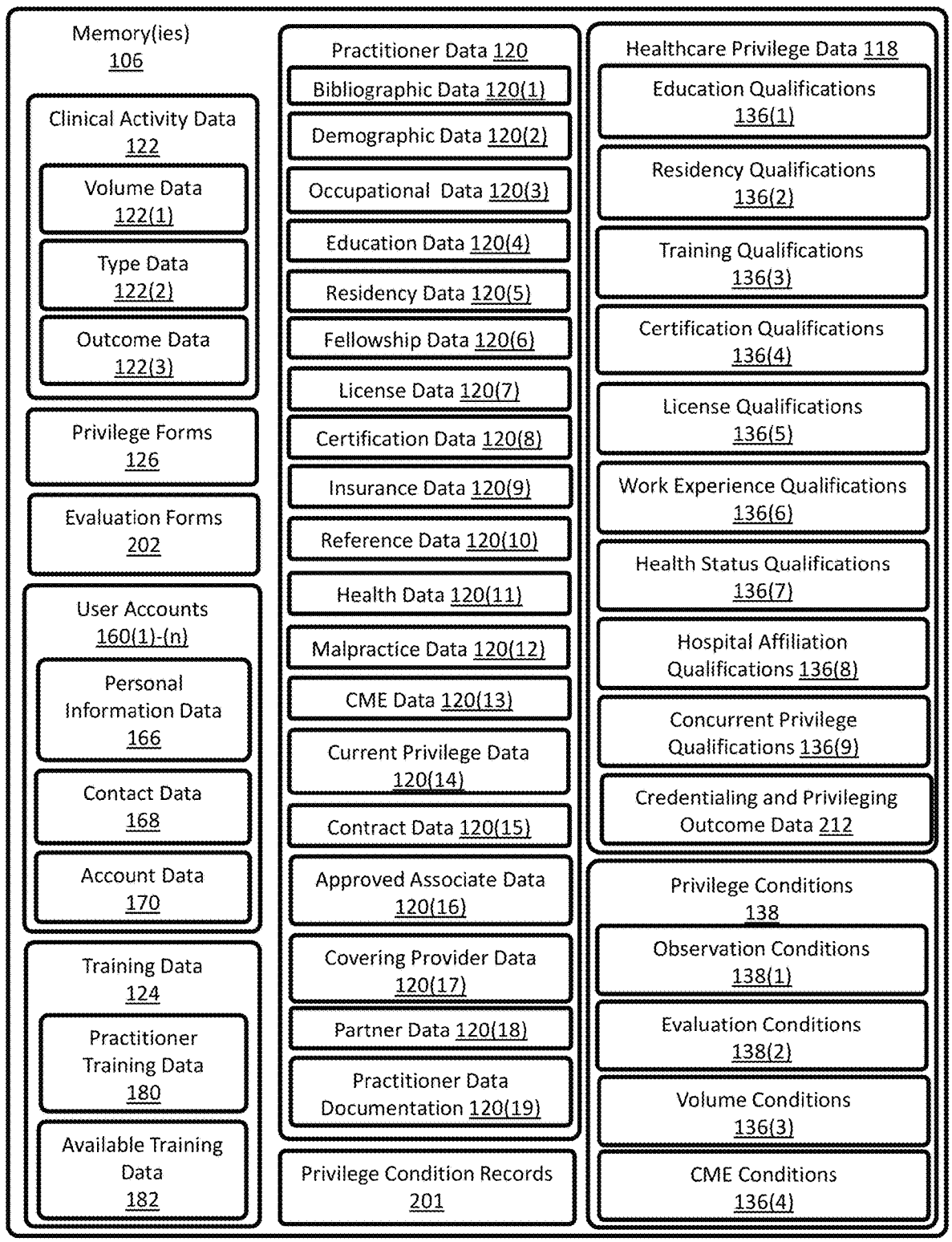
FIG. 2 is a schematic block diagram illustrating exemplary data that may be stored in the system shown in FIG. 1.

In some embodiments, the server 102 includes at least one memory 114. The at least one memory 114 may be a non-transitory storage device, such as a hard disk, flash memory, random access memory (RAM), or other types of non-transitory storage devices. The at least one memory 114 may store the account module 104(1), the credentialing and privileging module 104(2), the insights module 104(3), non-transitory computer-executable instructions 116, and other data. FIG. 2 illustrates an embodiment of the at least one memory 114 and the types of data that can be stored in the at least one memory 114. As shown in FIG. 2, the at least one memory 114 may also include healthcare privilege data 118, practitioner data 120, clinical activity data 122, training data 124, and a plurality of privilege forms 126(1)-(n).

Healthcare privilege data 118 includes data on one or more healthcare privileges 128. Healthcare privileges 128, or clinical privileges, are the authorization by a healthcare organization 130 to a healthcare practitioner 106(1) for the provision of healthcare services. Examples of healthcare privileges 128 include courtesy privileges, i.e., the privilege to occasionally treat or admit patients at a specific hospital; admitting privileges, i.e., the privilege to admit patients into a particular hospital; and surgical privileges, i.e., the privilege to provide specific inpatient or outpatient operations, procedures, or services at a given facility. Healthcare privileges 128 may also be organized into primary privileges, which are the basic healthcare privileges 128 granted to healthcare practitioners 106(1) practicing at a given facility, hospital, or hospital system, and supplementary privileges, which may be healthcare privileges 128 granted to healthcare practitioners 106(1) of a particular specialization.

Figure 3A:
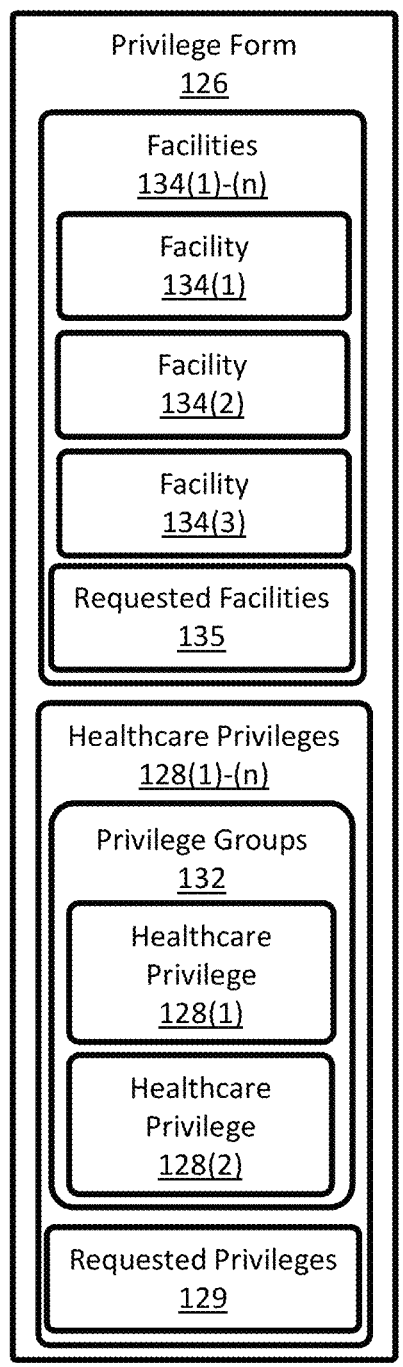
FIG. 3A is a schematic block diagram illustrating an exemplary embodiment of a privilege form for use with the system of FIG. 1.
Figure 3B:
FIG. 3B is a schematic block diagram illustrating an exemplary embodiment of a privilege form for use with the system of FIG. 1.

As shown in FIG. 3A, the one or more healthcare privileges 128(1)-(n) may be organized into privilege groups 132 (which may also be referred to as privilege clusters) including at least two healthcare privileges 128(1)-(2). The two or more healthcare privileges 128(1)-(n) in each privilege group 132 may be in the same field or specialty or may require the same or similar credentials in order to be performed by the healthcare practitioner 106(1) at one or more facilities 134(1)-(n). Examples of privilege groups 132 include congenital cardiac surgery privileges, human or mechanical heart transplantation, and transcatheter heart valve implantation.

Generally, healthcare privileges 128 are granted by the healthcare organization 130 to the healthcare practitioner 106(1) across one or more facilities 134(1)-(n). For example, a healthcare practitioner 106(1) may be granted the healthcare privilege 128 to perform a service at a single healthcare facility 134(1), a plurality (some or all) of facilities 134(1)-(n) within a single healthcare organization 130, or a plurality of facilities 134(1)-(n) across two or more healthcare organizations 130. In some embodiments, the healthcare privilege data 118 may include data on the healthcare privileges 128 that are available at one or more facilities 134.

Healthcare privilege data 118 may also include data about the required qualifications 136 and privilege conditions 138 for a healthcare practitioner 106(1) to be granted a particular healthcare privilege 128. For example, required qualifications 136 for a healthcare practitioner 106(1) to be granted a healthcare privilege 128 may include education qualifications 136(1), residency qualifications 136(2), training qualifications 136(3), certification qualifications 136(4), license qualifications 136(5), work experience (clinical experience) qualifications 136(6), health status qualifications 136(7), hospital affiliation qualifications 136(8), current privilege qualifications 136(9), and other qualifications. A health care organization 130 may also require that a healthcare practitioner 106(1) meet privilege conditions 138, or Focused Professional Practice Evaluation (FPPE), after being granted a healthcare privileges 128, such as observation conditions 138(1), evaluation conditions 138(2), minimum volume conditions 138(3), continuing medical education (CME) conditions 138(4), and other types of conditions. The required qualifications 136 and privilege conditions 138 required for a healthcare practitioner 106(1) to be granted a particular healthcare privilege 128 may vary based on whether the healthcare practitioner 106(1) is initially being granted the healthcare privilege 128, is being reappointed the healthcare privilege 128, or is being granted the healthcare privilege for a temporary period or mid-cycle.

Practitioner data 120 includes information about one or more healthcare practitioners 106(1). For example, practitioner data 120 may include bibliographic data 120(1), demographic data 120(2), occupational data 120(3), education data 120(4), residency data 120(5), fellowship data 120(6), license data 120(7), certification data 120(8), insurance data 120(9), reference data 120(10), health data 120(11), malpractice data 120(12), continuing medical education (CME) data 120(13), current privilege data 120(14), contract data 120(15), approved associate data 120(16), covering provider data 120(17), partner data 120(18), practitioner data documentation 120(19) or other relevant information and documentation therefore for one or more healthcare practitioners 106(1). In some embodiments, practitioner data 120 may include clinical activity data 122 and training data 124.

Bibliographic data 120(1) and/or demographic data 120(2) may include health practitioner's 106(1) name, age, sex, gender, race, background, or other bibliographic or demographic information. Occupational data 120(3) may include one or more facilities 134 that the healthcare practitioner 106(1) works at, the role or position of the healthcare practitioner 106(1) (e.g., a doctor, nurse, physician assistant, etc.), or one or more of the healthcare practitioner's 106(1) specialties (e.g., emergency medicine, neurology, oncology, etc.). Education data 120(4) may include information related to the healthcare practitioner's 106(1) graduation from an educational institution (undergraduate institution, medical school, dates attended, graduation date, degrees received, honors, etc.). Residency data 120(5) may include information related to residencies completed by the healthcare practitioner 106(1) (residency type, dates of completion, location, director, etc.). Fellowship data 120(6) may include information related to fellowships completed by the healthcare practitioner 106(1) (fellowship type, dates of completion, location, etc.). License data 120(7) may include information about medical licenses held by the healthcare practitioner 106(1) (e.g., jurisdictions where the healthcare practitioner 106(1) is licensed, dates of obtaining a license, expiration date of a license, issuer of the license) etc.). Certification data 120(8) may include information related to the healthcare practitioner's 106(1) certifications (e.g., a list of healthcare protocols that the healthcare practitioner 106(1) is certified in, dates for which the healthcare practitioner's 106(1) certifications expire, etc.)

Insurance data 120(9) may include information on malpractice insurance coverage obtained by the healthcare practitioner 106(1) (coverage type, coverage limits, coverage provider, etc.). Reference data 120(10) may include information about recommendations for the healthcare provider 106(1) (e.g., letters or recommendation, recommender name, recommender contact information, etc.). Health data 120(11) may include information about the health of the healthcare practitioner 106(1) (e.g., conditions which may inhibit ability to practice medicine, diagnosis dates, treatments, etc.). Malpractice data 120(12) may include information about malpractice claims or other lawsuits against the healthcare practitioner 106(1) (date of claim, reason for claim, claim status, outcome of claim, etc.). Continuing medical education (CME) data 120(13) may include information relating to the continuing medical education courses completed by the healthcare practitioner 106(1) (compliance with profession requirements, course types, course completion dates, etc.). Current privilege data 120(14) may include information about other healthcare privileges 128 contemporaneously held by the healthcare practitioner 106(1) (privilege type, corresponding facility, privilege status, restrictions, etc.). Contract data 120(15) may include information related to a contract between the healthcare practitioner 106(1) and the healthcare organization 130 for the healthcare practitioner 106(1) to provide healthcare services (services and facilities 134 covered by the contract, start date, contract term, etc.).

Approved associate data 120(16) may include supervising or collaborating relationships. Approved associate data 120(16) is generally, but not necessarily for holders of advanced practice degrees such as nurse practitioners, certified registered nurse anesthetists, and physician assistants. Covering provider data 120(17) can include data on partners or other providers or groups for call coverage for the healthcare practitioner 106(1). Partner data 120(18) may include data on a healthcare practitioner 106(1) partners in the group they are practicing with.

Clinical activity data 122 may include data about the clinical activities of one or more healthcare practitioners 106(1). For example, clinical activity data 122 may include information about the volume data 122(1), type data 122(2), outcome data 122(3), and other relevant information about the healthcare services provided by one or more healthcare providers 106(1)(1). In some embodiments, practitioner data 120 may include clinical activity data 122.

Training data 124 may include practitioner training data 124(1) related to trainings completed by the healthcare practitioner 106(1) (training courses, manufacturer required training, date completed, expiration date, etc.), CME data 120(13), and/or available training data 124 (2) about available trainings that may be used to allow healthcare practitioners 106(1) to acquire the training necessary to be granted healthcare privileges 128. In some embodiments, available training data 124 may include training schedules, training checklists, training videos, training materials, and other information about available trainings. In some embodiments, practitioner data 120 may include training data 124.

The plurality of privilege forms 126(1)-(n) may include pre-built, standard privilege forms 126 or may include privilege forms 126 customized for a specific facility, hospital, or healthcare organization. The plurality of privilege forms 126 may be organized into one or more privilege categories 140. As shown in FIG. 3A, the one or more privilege categories 140 may include at least one of specialty categories 140(1) (e.g., pediatrics, cardiology, dermatology, etc.), care setting categories 140(2) (e.g., ambulatory, post-acute, surgery centers, etc.), practitioner categories 140(3) (advanced practice practitioner, medical doctor, doctor of osteopathic medicine, nurse practitioner, etc.), or procedure categories 140(4) (in-patient, out-patient, invasive, non-invasive, etc.).

Figure 4:
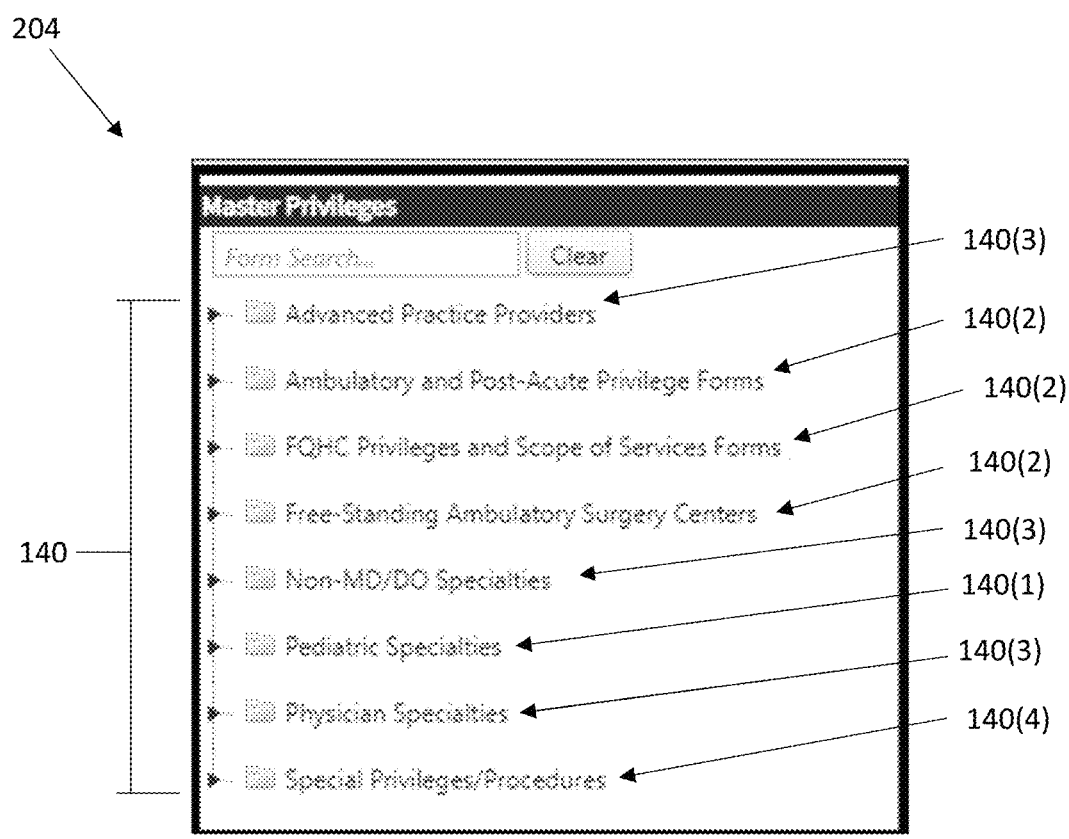
FIG. 4 is a front view illustrating an exemplary web portal for credentialing and privileging of healthcare practitioners displayed on a user device.

FIG. 4 shows one embodiment of a privilege form 126 for use with the systems and method of the present disclosure. Each privileges form 126 may correspond to the one or more healthcare privileges 128 in the healthcare privilege data 118. For example, each privilege form 126 may correspond to one or more primary healthcare privileges 128 or one or more specialty healthcare privileges 128. For example, one privilege form 126 may cover privilege groups 132 such as cardiac procedures or general thoracic procedures or may cover individual healthcare privileges 128 such as exploratory thoracotomy.

Figure 5A:
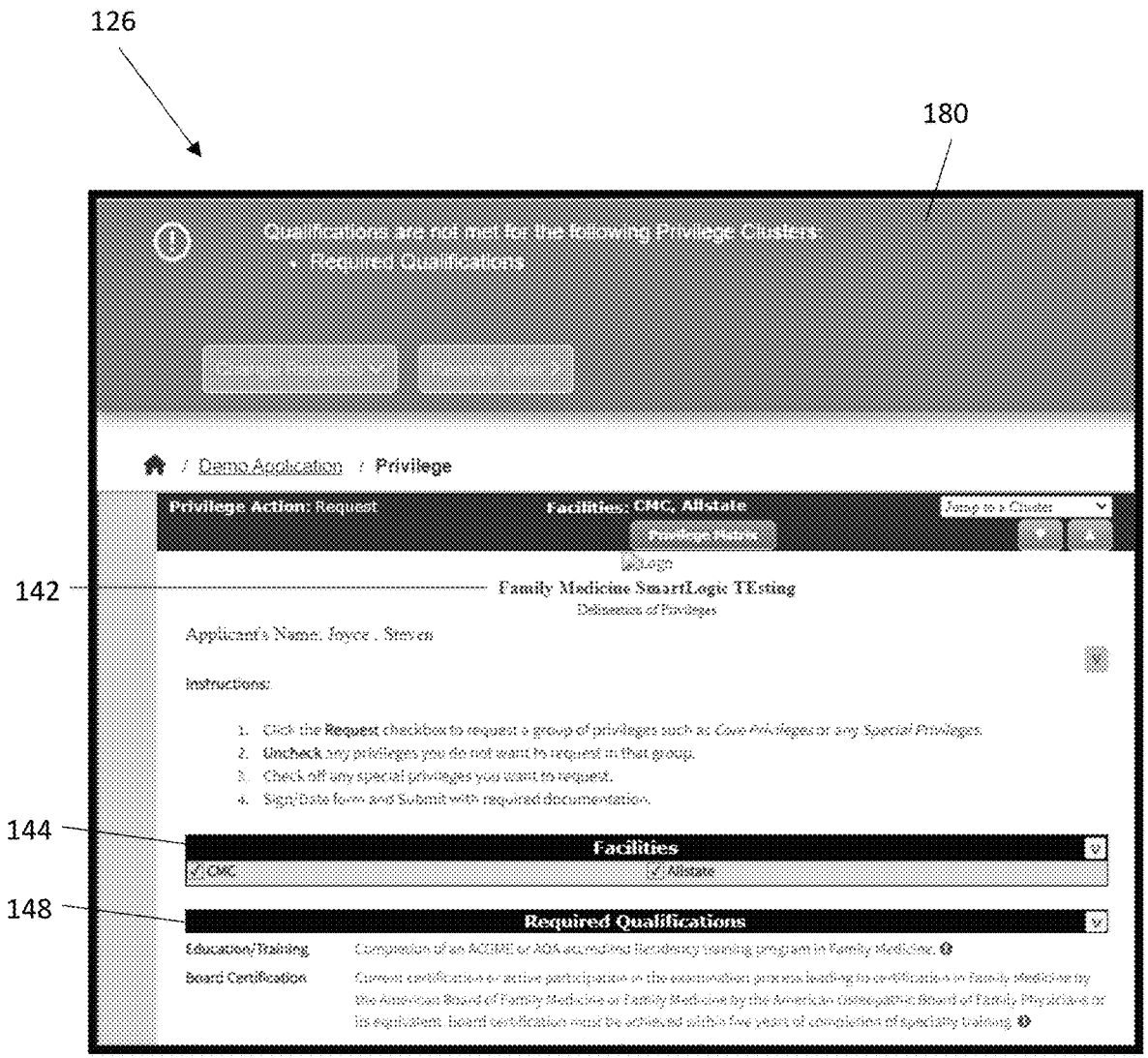
FIG. 5A is a front view illustrating an exemplary web portal displaying one embodiment of a privilege form for credentialing and privileging of healthcare practitioners.
Figure 5B:
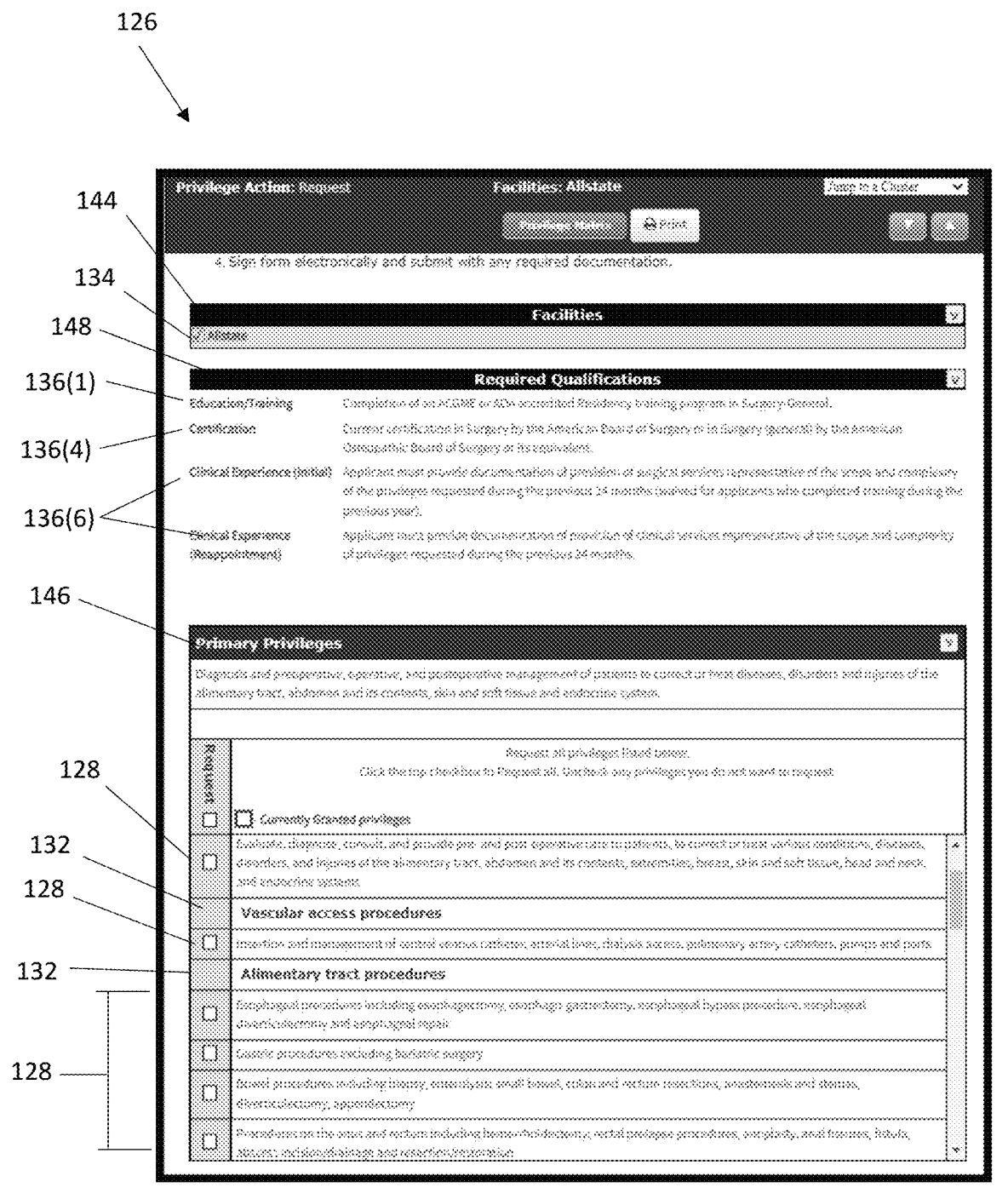
Figure 5C:
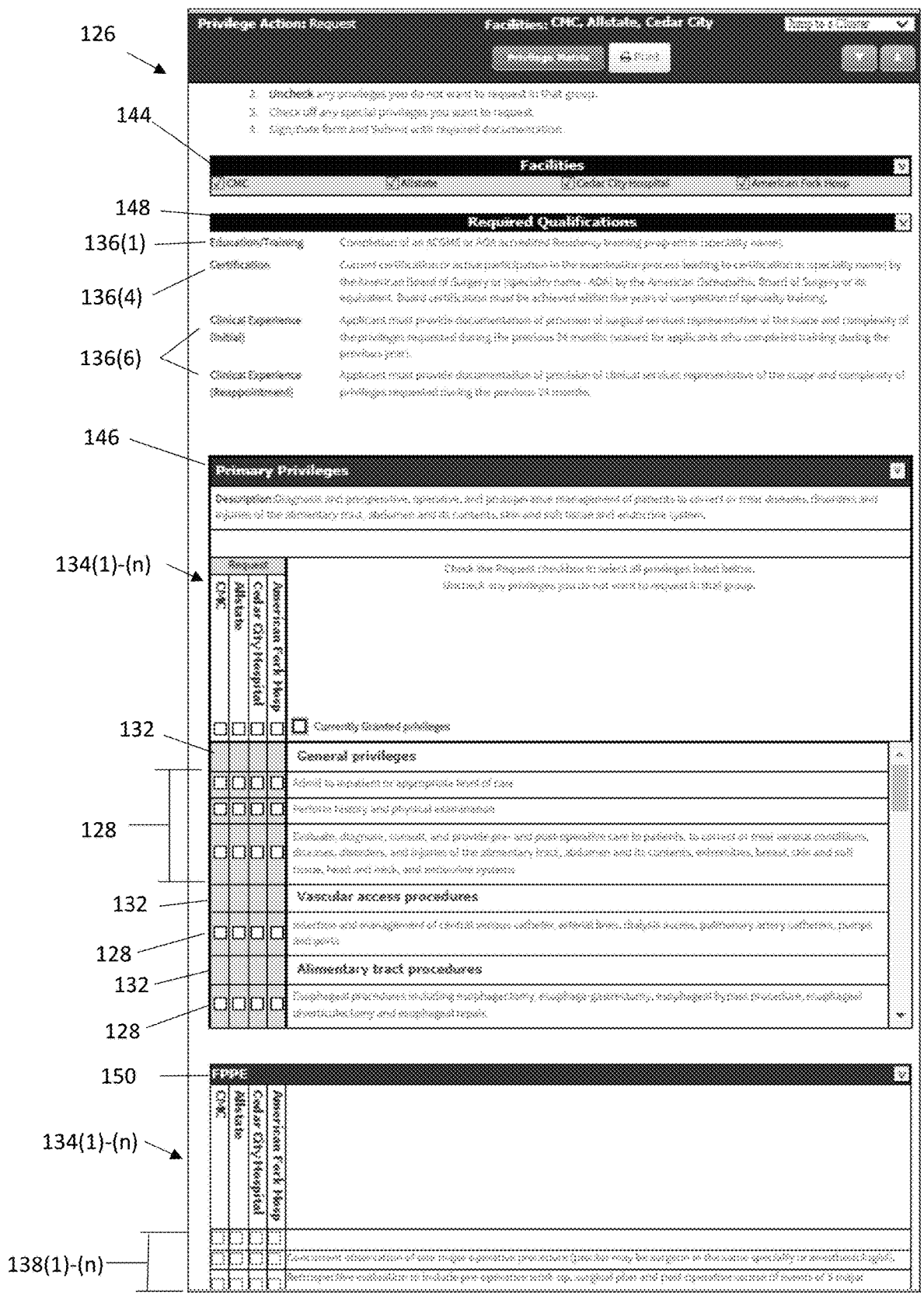
FIG. 5C is a front view illustrating yet another exemplary web portal displaying one embodiment of a privilege form for credentialing and privileging of healthcare practitioners.

Each privilege form 126 may have a similar structure. As shown in FIGS. 5A-5C. each privilege form 126 may have a privilege form name 142, a facilities section 144 listing one or more facilities 134, a privileges section 146 listing one or more available healthcare privileges 128, a required qualifications sections 148 listing one or more required qualifications 136 for being granted the one or more healthcare privileges 128 listed in the privileges sections 146, and a conditions sections 150 listing one or more privilege conditions 138 for maintaining the one or more healthcare privileges 128 listed in the privileges sections 150.

Figure 6:
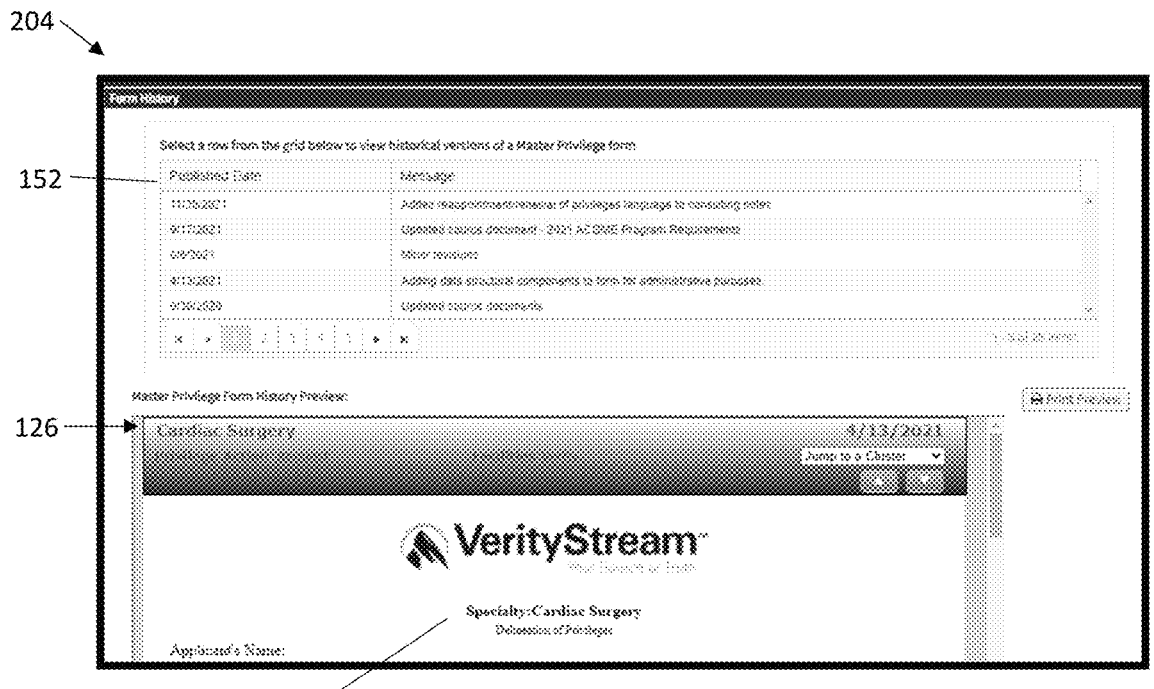
FIG. 6 is a front view illustrating still another exemplary web portal displaying one embodiment of a privilege form history.
Figure 7:
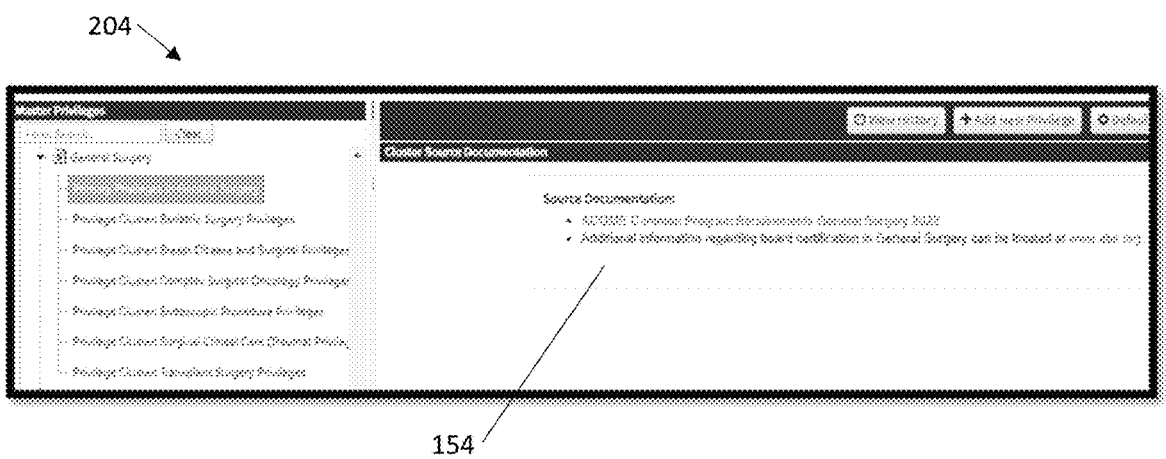
FIG. 7 is a front view illustrating another exemplary web portal displaying one embodiment of source documentation.
Figure 8:
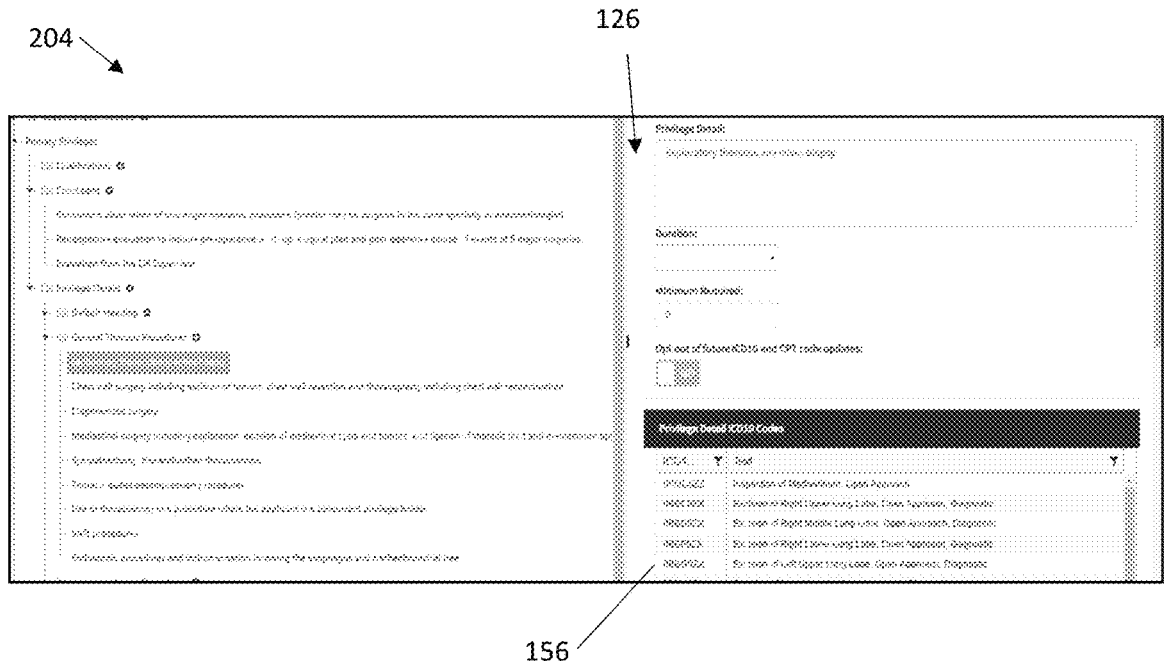
FIG. 8 is a front view illustrating yet another exemplary web portal displaying one embodiment of a privilege form including medical codes.

Each privilege form 126 may also include a privilege form history 152, source documentation 154 associated with the one or more healthcare privileges 128(1)-($n$) or privilege groups 132 included in the privilege form 126, and one or more medical codes 156 associated with the one or more healthcare privileges 128(1)-($n$). As shown in FIG. 6 each privilege forms 126 may include a privilege form history 152 that include data on revisions, updates, or other changes made to the privilege form 126. The privilege forms 126 may also include source documentation 154 that provides support for the required qualifications 136 or privilege conditions 140 included in the privilege form 126, as shown in FIG. 7. Each privilege form 126 may also include one or more medical codes 156 associated with the one or more healthcare privileges 128. The one or more medical codes 156 may be ICD-10 codes, CPT codes, or both. For example, as shown in FIG. 8, a privilege form 126 for the privilege 128 of exploratory thoracotomy may include ICD-10 codes such as 0WJC0ZZ (inspection of mediastinum, open approach), 0BBC0ZX (excision of right upper lung lobe, open approach, diagnostic), 0BBD0ZX (excision of right middle lung lobe, open approach, diagnostic), 0BBF0ZX (excision of right lower lung lobe, open approach, diagnostic), 0BBG0ZX (excision of left upper lung lobe, open approach, diagnostic), etc.

In some embodiments, the system 100 may include a data network 112. The data network 112 may allow the server 102, user devices 110(1)-($n$), and other devices to be in data communication. In one embodiment, the data network 112 may include a local area network (LAN), wide area network (WAN), the Internet, or other network. The data network 112 may include wired or wireless communication. The server 102 and the one or more user devices 110(1)-($n$) may be in data communication with each other via the data network 112. The server 102 and the one or more user devices 110(1)-($n$) may send data over the data network 112 and may receive data over the data network 112.

In some embodiments, the system 100 may include one or more user devices 110(1)-($n$). The one or more user devices 110(1)-($n$) may include a personal computer, a tablet computer, a smartphone, or other computing device. The one or more user devices 110(1)-($n$) may include software, such as a software application (app), that may perform functionality, such as communicating with the server 102. In some embodiments, some of the functionality of the one or more modules 104(1)-(3) of the server 102 may be performed by the one or more user devices 110(1)-($n$). The one or more user device 110(1)-($n$) may send data to the server 102 and may receive data from the server 102. The one or more user devices 110(1)-($n$) may include graphic user interfaces and other input devices and output devices. The one or more user devices 110(1)-($n$) may display various representations of data based on the data received from the server 102 on output devices such as computer screens. The user device may receive user input via input devices (i.e., keyboards, microphones, etc.) and send data to the server 102 based on the user input. The user input may include input to configure the one or more modules 104(1)-(3) of the server 102.

The server 102 may include at least one processor 158 for executing the non-transitory computer-executable instructions 116 or processing other data. Although the at least one processor 158 is described herein as executing the non-transitory computer-executable instructions 116, it is understood that the actions of the at least one processor 158 may be imputed to the server 102 or the system 100. In some embodiments, the one or more modules 104(1)-(3) may include software installed on or executed by the at least one processor 158.

In some embodiments, the server 102 may include an account module 104(1). In one embodiment, the account module 104(1) may store, configure, or process data associated with one or more user accounts 160(1)-($n$). User accounts 160(1)-($n$) may store data associated with user of the system. A user may include a person that works at a healthcare facility or works for a health care organization. Example users include but are not limited to healthcare practitioner 106(1), a reviewer 106(2), and an administrator 106(3). A healthcare practitioner 106(1) may be a doctor, physician's assistant, nurse practitioner, or other type of healthcare worker that may make a privilege request 162 to be granted healthcare privileges 128 at one or more healthcare facilities 134. A reviewer 106(2) may be a user that may review the healthcare practitioner's 106(1) privilege request and make recommendations to grant or deny the request, such as department chiefs or chairs in a healthcare organization 130. An administrator 106(3) may review the healthcare practitioner's 106(1) privilege request and the reviewer's 106(2) recommendation and decide whether to grant or deny the healthcare privileges 128 to the healthcare practitioner 106(1). For example, the administrator 106(3) may include one or more member of a medical executive board.

User accounts 160(1)-($n$) may store data about the users 106(1)-(3). In some embodiments, the data stored in the user accounts 160(1)-($n$) of healthcare practitioners 106(1) may include or overlap with practitioner data 120. In other embodiments, practitioner data 120 may be stored separately from the account module 104(1) or the server 102. User accounts 160(1)-($n$) may include personal information data. Personal information data 166 may include the user's name, age, sex, or other personal data. User accounts 160(1)-($n$) may include contact data 168. Contact data 168 may include the user's address, phone number, email address, or other contact information. User accounts 160(1)-($n$) may store account data 170. Account data 170 may include information about the user's account type, account history, and other account-specific information. Different users 106(1)-(3) may have different account types (i.e., healthcare practitioner account, reviewer account, administrator account, etc.). The account types may determine the information shown to or accessible by the users 106(1)-(3), the actions that can be taken by the users 106(1)-(3), and the information requested from the users 106(1)-(3).

In one embodiment, the account module 104(1) may receive data related to one or more users 106(1)-(3) of one or more user accounts 160(1)-($n$). The account module 104(1) may update the user accounts 160(1)-($n$) based on the received data. For example, as described below, in response to the account module 104(1) receiving data indicating that a healthcare practitioner 106(1) has completed at least a portion of a certification program, the account module 104(1) may update the certification data 120(8) for the healthcare practitioner 106(1). In some embodiments, the account module 104(1) may output data stored in one or more user accounts 160(1)-(*n*). For example, the account module 104(1) may send account data 170 to the user device 110(1) to be viewed by a user 106(1).

Credentialing and Privileging

In one embodiment, the server 102 may include the credentialing and privileging module 104(2). The credentialing and privileging module 104(2) may be configured to facilitate the credentialing and privileging of the healthcare practitioner 106(1). For example, the credentialing and privileging module 104(2) may include non-transitory computer-executable instructions 116 that, when executed by the at least one processor 158, cause the credentialing and privileging module 104(2) to carry out, perform, or implement, one or more steps, actions, operations, or the like. Although such steps, actions, or operations may be described as being performed or implemented by the credentialing and privileging module 104(2), it is understood that such operations may be described as being performed or implemented by the at least one processor 158, the server 102, or the system 100.

In one embodiment, the credentialing and privileging module 104(2) may receive a form request 174 from a healthcare practitioner 108. The form request 174 may include a request to receive a dynamic privilege form 174 for one or more privilege categories 140 at one or more facilities 134(1)-(*n*). As discussed herein, the one or more categories may include at least one of specialty categories 140(1), care setting categories 140(2), practitioner categories 140(3), and procedure categories 140(4). The one or more facilities 134(1)-(*n*) may be a single healthcare facility 134 as shown in FIG. X, a plurality of facilities 134 within a single healthcare system, or a plurality of facilities 134(1)-(*n*) across two or more healthcare systems. The healthcare practitioner 106(1) may create the form request 174 using a user device 110. For example, the credentialing and privileging module 104(2) may provide a list of one or more privilege categories 140 for the healthcare practitioner 108 to choose from as shown in FIG. 8 and/or a list of one or more facilities 134 for the healthcare practitioner 106(1) to choose from.

The credentialing and privileging module 104(2) may send the privilege form 126 to the healthcare practitioner 106(1) in response to the form request 174. The credentialing and privileging module 104(2) may send the privilege form 126 through the data network 112 to the user device 110 of the healthcare practitioner 106(1). In some embodiments, the credentialing and privileging module 104(2) may select a privilege form 126 from the plurality of privilege forms 126(1)-(*n*) to send to the healthcare practitioner 106(1). In other embodiments, the credentialing and privileging module 104(2) may generate a dynamic privilege form 126(1) based on the form request 174. When the at least one memory 114 stores a plurality of privilege forms 126(1)-(*n*), the dynamic privilege form 126(1) may be based on one or more of the plurality of privilege forms 126(1)-(*n*). The dynamic privilege form 126(1) is "dynamic" in the sense that the credentialing and privilege model 104(2) customizes the dynamic privilege form 126(1) based on the form request 174, which may include modifying, altering or changing one or more of the plurality of privilege forms 126(1)-(*n*).

The privilege form 126 sent to the healthcare practitioner 106(1) may include one or more healthcare privileges 128(1)-(*n*) and one or more facilities 134(1)-(*n*) for selection by the healthcare practitioner 106(1) as shown in FIGS. 5B-5C. The one or more healthcare privileges 128(1)-(*n*) in the privilege form 126 sent to the healthcare practitioner 106(1) may be in the one or more privilege categories 140(1)-(5) selected by the healthcare practitioner 106(1) in the form request 174. For example, if the healthcare practitioner 106(1) selects the specialty category 140(1) of cardiology, the one or more healthcare privileges 128(1)-(*n*) displayed in the privilege form 126 may be privileges 128(1)-(*n*) in the field of cardiology. The privilege form 126 may include one or more privilege groups 132. At least two healthcare privilege 128(1)-(2) of the one or more healthcare privileges 128(1)-(*n*) in the privilege form 126 sent to the healthcare practitioner 106(1) may be organized into the one or more privilege groups 132. The two or more healthcare privileges 128(1)-(2) in each privilege group 132 may require the same qualifications or conditions in order to be performed by the healthcare practitioner 106(1) at the one or more facilities 134 in the privilege form 126. Moreover, the one or more facilities 134(1)-(*n*) in the privilege form 126 may include or be based on the one or more facilities 134(1)-(*n*) of the form request 174.

Figure 9:
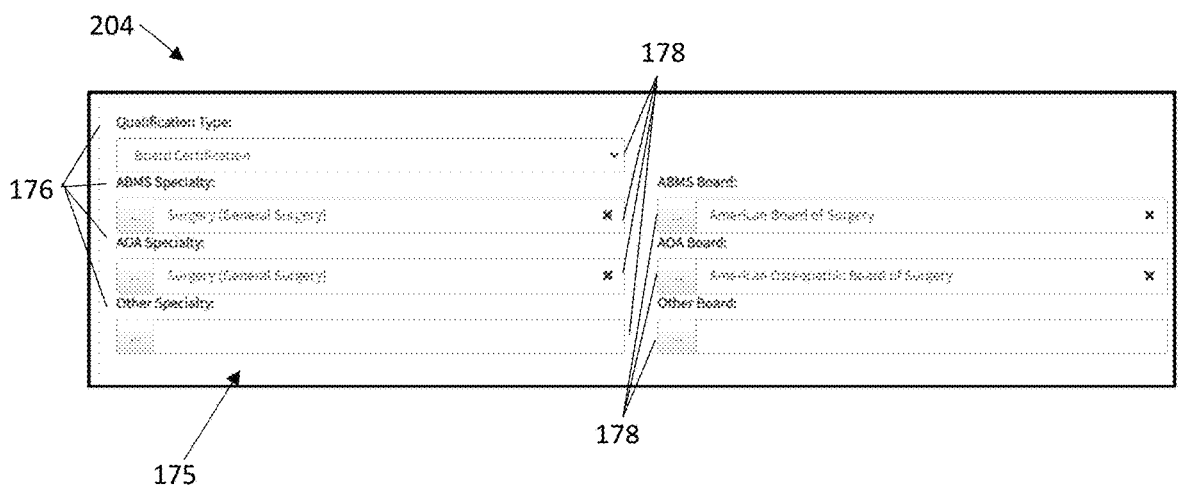
FIG. 9 is a front view illustrating still another exemplary web portal displaying one embodiment of a credential form including prompts for the credentials of a healthcare practitioner and credential responses.

As shown in FIGS. 3A and 9, the memory may include a credential form 175 having a plurality of prompts 176 for the credentials of the healthcare practitioner 106(1). The plurality of prompts 176 may correspond to the required qualifications 136 for a healthcare practitioner 106(1) to be granted a particular healthcare privilege 128. For example, the plurality of prompts 176 may include one or more of an education prompt 176(1), a residency prompt 176(2), a training prompt 176(3), a work experience (clinical experience) prompt 176(4), a certification prompt 176(5), a license prompt 176(6), a health status prompt 176(7), a hospital affiliation prompt 176(8), a current privilege prompt 176(9), and other prompts. In some embodiments, the plurality of prompts 176 may include an education prompt 176(1), a training prompt 176(2), a certification prompt 176(3), and a clinical activity prompt 176(4). The plurality of prompts 176 for the credentials of the healthcare practitioner 106(1) may be tailored based on the one or more privilege categories 140 and one or more facilities 134(1)-(*n*) of the form request 174.

Using the user device 110, the healthcare practitioner 106(1) may be able to select privileges 128(1)-(*n*) from the one or more privileges 128(1)-(*n*) in the privilege form that the healthcare practitioner 106(1) would like to request. The healthcare practitioner 106(1) may be able to select some or all of the one or more privileges 128(1)-(*n*) in the privilege form. When the privilege form 126 only includes one facility 134, the healthcare practitioner 106(1) may only be able to select the one or more healthcare privileges 128(1)-(*n*) that they would like to request. When the privilege form 126 includes two or more facilities 134(1)-(*n*), the healthcare practitioner 106(1) may be able to select some or all of the one or more facilities 134(1)-(*n*) of the privilege form 126 to request the one or more privileges 128(1)-(*n*) at, as shown in FIG. X.

The healthcare practitioner 106(1) may also be able to input one or more credential responses 178 to the plurality of prompts 176 into the credential form 175 As shown in FIGS. 3A and 9, the one or more credential responses 178 may correspond to the plurality of prompts 176 in the privilege form 126. For example, one or more credential responses 178 may include one or more of an education response 178(1), a residency response 178(2), a training response 178(3), a work experience (clinical experience) response 178(4), a certification response 178(5), a license response 178(6), a health status response 178(7), a hospital affiliation response 178(8), a current privilege response 178(9), and other responses. In some embodiments, the one or more credential responses 178 may include an education response 178(1), a training response 178(2), a certification response 178(3), and a work experience response 178(4). The healthcare practitioner 106(1) may input the one or more credential responses 178 into the credential form 175 using one or more input devices of the user device 110.

In some embodiments, the credentialing and privileging module 104(2) may generate one or more credential responses 178 to the plurality of prompts 176. In embodiments of the system 100 in which the at least one memory 114 stores practitioner data 120 or clinical activity data 122, the credentialing and privileging module 104(2) may generate one or more credential responses 178 to the plurality of prompts 176 based on the practitioner data or clinical activity data. For example, the credentialing and privileging module 104(2) may generate one or more credential responses 178 based on clinical activity data 122 including information on the number and type of healthcare services provided by the healthcare practitioner 106(1) and practitioner data 120 including education data 120(4), training data 124, and certification data 120(8). In embodiments where the credentialing and privileging module 104(2) generates one or more credentials responses 178, the generated one or more credential responses 178 may be prepopulated into the privilege form 126 sent to the healthcare practitioner 106(1). The healthcare practitioner 106(1) may be able to modify the generated one or more credential responses 178 if they are incomplete, outdated, or have other inaccuracies.

In embodiments where the at least one memory 114 stores source documentation 154 for each privilege 128 or privilege group 132, the healthcare practitioner 106(1) may request to see the source documentation 154. For example, the healthcare practitioner 106(1) may request to see the source documentation by clicking on a link in the privilege form as shown in FIG. 7. The credentialing and privileging module 104(2) may receive the request for source documentation 154 for one or more of the privilege groups from the healthcare practitioner 106(1) via the data network. The credentialing and privileging module 104(2) may then send the source documentation for the one or more privilege groups to the healthcare practitioner 106(1).

The healthcare practitioner 106(1) may submit the privilege form 126 and/or the credential form 175 to the credentialing and privileging module 104(2) through the data network 112. The credentialing and privileging module 104(2) may receive the privilege form 126 from the healthcare practitioner 106(1) via the data network 112. The privilege form 126 received by the credentialing and privileging module 104(2) may include the requested healthcare privileges 129 from the one or more healthcare privileges 128(1)-(n), and the requested facilities 135 from the one or more facilities 134(1)-(n). The credential form 175 may include the one or more credential responses 178. The privilege form 126 may then be sent to one or more other users 106(1)-(3).

The system of the present disclosure may facilitate a multi-stage privileging review, i.e., a review performed by one or more reviewers 106(2) and one or more administrators 106(3). In some embodiments, the credentialing and privileging module 104(2) may identify and assign the reviewer(s) 106(2) and administrator(s) 106(3) for a privilege request. The credentialing and privileging module 104(2) may identify and assign the reviewer(s) 106(2) and administrator(s) 106(3) based on the role of such individuals within a healthcare organization 130 and facility 134 and based on requested healthcare privileges 129 and requested facilities 135. The credentialing and privileging module 104(2) may also determine the hierarchy or sequence in which the reviewer(s) 106(2) and administrator(s) 106(3) review or receive the privilege request.

In some embodiments, the credentialing and privileging module 104(2) may analyze the one or more credential responses 178 of the healthcare practitioner 106(1) prior to sending them to the reviewer 106(2). In such embodiments, the at least one memory 114 may store healthcare privilege data 118 including information on required qualifications 136 required for a healthcare practitioner 106(1) to perform each of a plurality of healthcare privileges 128(1)-(n) at one or more facilities 134(1)-(n). The credentialing and privileging module 104(2) may compare the one or more credential responses 178 to the required qualifications 136 for the requested healthcare privileges 129 at the requested facilities 135.

As shown in FIG. 5A, if the one or more credential responses 178(1)-(n) are less than the required qualifications 136, the credentialing and privileging module 104(2) may send a required qualifications notification 180 to the healthcare practitioner 106(1) and/or the reviewer 106(2) that the one or more credential responses 178 are less than the required qualifications 136 for the requested healthcare privileges 129. Further, the credentialing and privileging module 104(2) may send the privilege form 126 with the requested healthcare privileges 129 and the requested facilities 135 along with the credential form 175 including the one or more credential responses 178 back to the healthcare practitioner 106(1). The healthcare practitioner 106(1) may modify at least one of the requested healthcare privileges 129, the requested facilities 135, and the one or more credential responses 178 from the healthcare practitioner 106(1) in response to the required qualifications notification 180. The credentialing and privileging module 104(2) may receive the privilege form 126 and/or credential form 175 with the modifications to at least one of the requested healthcare privileges 129, the requested facilities 135, and the one or more credential responses 178 from the healthcare practitioner 106(1).

In some embodiments, the credentialing and privileging module 104(2) may verify the one or more credential responses 178 in the credential form 175. In such embodiments, the at least one memory 114 further stores practitioner data 120 for the healthcare practitioner 106(1) and clinical activity data 122 including information on healthcare services provided by the healthcare practitioner 106(1). The credentialing and privileging module 104(2) may compare the one or more credential responses 178 to the practitioner data 120 and clinical activity data 122 to validate the one or more credential responses 178. As used herein, "validate" may mean determining that the one or more credential responses 178 are accurate based on the practitioner data 120 and clinical activity data 122. If the one or more credential responses 178 cannot be validated using the practitioner data 120 and clinical activity data 122, the credentialing and privileging module 104(2) may send a documentation request to the healthcare practitioner 106(1). The documentation request 182 may include a request for practitioner data documentation 120(19) to validate the one or more credential responses 178.

After receiving the privilege form 126 from the healthcare practitioner 106(1), the credentialing and privileging module 104(2) may send the privilege form 126, including the requested healthcare privileges 129 and the requested facilities 135 as well as the credential form 175 with the one or more credential responses 178 to the reviewer 106(2). The credentialing and privileging module 104(2) sends the privilege form 126 and credential form 175 to the user device 110 of the reviewer 106(2) via the data network 112. The reviewer 106(2) may review the privilege form 126 and credential form 175 on a screen or other visual output device of the user device 110.

If the reviewer 106(2) decides that further information is needed from the healthcare practitioner 106(1) before granting or denying one or more of the requested healthcare privileges 129 at one or more of the requested facilities 135, the reviewer 106(2) may submit an information request 184 for further information about the healthcare practitioner 106(1). The reviewer 106(2) may submit the information request 184 on the user device. The credentialing and privileging module 104(2) may receive the information request 184 from the reviewer 106(2) via the data network 112. The credentialing and privileging module 104(2) may send the information request 184 and the privilege form 126 with the requested healthcare privileges 129 and the requested facilities 135 along with the credential form 175 with the one or more credential responses 178 to the healthcare practitioner 106(1). Among other benefits, sending the privilege form 126 and the credential form 175 to the healthcare practitioner 106(1) with the requested healthcare privileges 129, the requested facilities 135, and the one or more credential responses 178 included prevents the healthcare practitioner 106(1) from re-completing the privilege form 126 and credential form 175, which saves times and reduces the possibility of further errors.

If the reviewer 106(2) decides that the privilege form 126 contains sufficient information to grant or deny one or more of the requested healthcare privileges 129 at one or more of the requested facilities 135, the reviewer 106(2) may submit on the user device 110 a privilege recommendation 186 to grant or deny one or more of the requested healthcare privileges 129 at one or more of the requested facilities 135. The privilege recommendation 186 may be to grant all of the requested healthcare privileges 129 at all of the requested facilities 135, deny all of the requested healthcare privileges 129 at all requested facilities 135, or to grant a portion of the requested healthcare privileges 129 at one or more of the requested facilities 135 and deny a portion of the requested healthcare privileges 129 at one or more of the requested facilities 135. The credentialing and privileging module 104(2) may receive the privilege recommendation 186 to grant or deny one or more of the requested healthcare privileges 129 at one or more of the requested facilities 135 from the reviewer via the data network 112.

The credentialing and privileging module 104(2) may send the privilege recommendation 186 to grant or deny one or more of the requested healthcare privileges 129 at one or more of the requested facilities 135 to an administrator 106(3). The credentialing and privileging module 104(2) may also send the privilege form 126 with the requested healthcare privileges 129, the requested facilities 135, and the one or more credential responses 178 to the healthcare practitioner 106(1) to an administrator 106(3). The credentialing and privileging module 104(2) may send the privilege recommendation 186 of the administrator 106(3) and the privilege form 126 to the user device 110 of the administrator 106(3) via the data network 112. The administrator 106(3) may review the privilege form 126 on the screen or other visual output device of the user device 110.

In some embodiments, the credentialing and privileging module 104(2) may implement a neural network 188. The neural network 188 may be computer algorithms modeled loosely after the human brain and can recognize patterns, learn nonlinear rules, and define complex relationships among data. The credentialing and privileging module 104(2) may analyze one or more of healthcare privilege data 118, practitioner data 120, clinical activity data 122, and the privilege form 126 received from the healthcare practitioner 106(1) using the neural network 188.

The credentialing and privileging module 104(2) may generate a privilege recommendation 186 based on the analysis of the healthcare privilege data 118, practitioner data 120, clinical activity data 122, and the privilege form 126 received from the healthcare practitioner 106(1) using the neural network 188. In some embodiments, the privilege recommendation 186 may be a recommendation for the healthcare practitioner 106(1) to request one or more additional healthcare privileges 128(1)-($n$) at one or more facilities 134(1)-($n$). The credentialing and privileging module 104(2) may send such a privilege recommendation 186 to the healthcare practitioner 106(1).

In other embodiments, the privilege recommendation 186 may be a recommendation to grant or deny one or more of the requested healthcare privileges 129 at the one or more of the requested facilities 135, a recommendation to modify the healthcare privileges 128(1)-($n$) granted to the healthcare practitioner 106(1), a recommendation to renew the healthcare privileges 128(1)-($n$) granted to the healthcare practitioner 106(1), or a combination of such recommendations. The credentialing and privileging module 104(2) may send such a privilege recommendation 186 to the reviewer 106(2) or the administrator 106(3). If the privilege recommendation 186 is sent to the reviewer 106(2), the reviewer 106(2) may modify the privilege recommendation 186 before the privilege recommendation 186 is sent to the administrator 106(3). The credentialing and privileging module 104(2) may receive the modified privilege recommendation 186 from the reviewer 106(2) and send the modified privilege recommendation 186 to the administrator 106(3) via the data network 112.

If the administrator 106(3) decides that further information is needed from the healthcare practitioner 106(1) before granting or denying one or more of the requested healthcare privileges 129 at one or more of the requested facilities 135, the administrator 106(3) may submit an information request 184 on the administrator's 106(3) user device 110. The credentialing and privileging module 104(2) may receive the information request 184 from the administrator 106(3) via the data network 112. The credentialing and privileging module 104(2) may send the information request 184, the privilege form 126 with the requested healthcare privileges 129 and the requested facilities 135, and the credential form 175 with the one or more credential responses 178 to the healthcare practitioner 106(1). In some embodiments, the administrator 106(3) may temporarily grant one or more of the requested healthcare privileges 129 at one or more of the requested facilities 135. For example, the administrator 106(3) may temporarily grant one or more of the requested healthcare privileges 129 at one or more of the requested facilities 135 while awaiting a response to the information request 184. The credentialing and privileging module 104(2) may receive the temporary privilege grant 191 of one or more of the requested healthcare privileges 129 at one or more of the requested facilities 135. For example, the credentialing and privileging module 104(2) may receive a temporary privilege grant 191 of all of the requested healthcare privileges 129 at all of the request facilities 134(1)-($n$)

or for a portion of the requested healthcare privileges 129 at some or all of the requested facilities 135.

If the administrator decides that the privilege form 126 demonstrates that the healthcare practitioner 106(1) meets the required qualifications 136 to receive the one or more of the requested healthcare privileges 129 at one or more of the requested facilities 135, the administrator 106(3) may submit a privilege grant 192 of the one or more of the requested healthcare privileges 129 at one or more of the requested facilities 135. The credentialing and privileging module 104(2) may receive the privilege grant 192 of one or more of the requested healthcare privileges 129 at one or more of the requested facilities 135. The privilege grant 192 may be for all of the requested healthcare privileges 129 at all of the requested facilities 135 or for a portion of the requested healthcare privileges 129 at some or all of the requested facilities 135.

If the administrator 106(3) decides that the privilege form 126 does not demonstrate that the healthcare practitioner 106(1) meets the requirements to receive the one or more of the requested healthcare privileges 129 at one or more of the requested facilities 135, the administrator 106(3) may submit a privilege denial 190 of the one or more of the requested healthcare privileges 129 at one or more of the requested facilities 135. The credentialing and privileging module 104(2) may receive the privilege denial 190 of one or more of the requested healthcare privileges 129 at one or more of the requested facilities 135. The privilege denial 190 may be for all of the requested healthcare privileges 129 at all of the requested facilities 135 or for a portion of the requested healthcare privileges 129 at some or all of the requested facilities 135.

In response to receiving the privilege denial 190 of one or more of the requested healthcare privileges 129 at one or more of the requested facilities 135, the credentialing and privileging module 104(2) may send the privilege form 126 with the requested healthcare privileges 129 and the requested facilities 135 along with the credential form 175 with the one or more credential responses 178 back to the healthcare practitioner 106(1). The healthcare practitioner 106(1) may modify at least one of the requested healthcare privileges 129, the requested facilities 135, and the one or more credential responses 178 from the healthcare practitioner 106(1) in response to the privilege denial 190. The credentialing and privileging module 104(2) may receive the privilege form 126 and/or credential form 175 with the modifications to at least one of the requested healthcare privileges 129, the requested facilities 135, and the one or more credential responses 178 from the healthcare practitioner 106(1). The credentialing and privileging module 104(2) may then resend the privilege form 126 and/or credential form 175 with the modifications to at least one of the requested healthcare privileges 129, the requested facilities 135, and the one or more credential responses 178 to the administrator 106(3).

If the administrator 106(3) decides that the privilege form 126 demonstrates that the healthcare practitioner 106(1) has required qualifications 136 to receive the one or more of the requested healthcare privileges 129 at one or more of the requested facilities 135, the administrator 106(3) may submit a privilege grant 192 of the one or more of the requested healthcare privileges 129 at one or more of the requested facilities 135. The credentialing and privileging module 104(2) may receive the privilege grant 192 of one or more of the requested healthcare privileges 129 at one or more of the requested facilities 135(1)-(n). The privilege grant 192 may be for all of the requested healthcare privileges 129 at all of the requested facilities 135 or for a portion of the requested healthcare privileges 129 at some or all of the requested facilities 135.

The credentialing and privileging module 104(2) may allow the healthcare practitioner 106(1) to request an exemption to the required qualifications 136 and/or privilege conditions 138 required for the healthcare practitioner 106(1) to be granted one or more healthcare privileges 128(1)-(n). The credentialing and privileging module 104(2) may receive the exemption request 194 from the from the healthcare practitioner 106(1). The exemption request 194 may identify one or more of the required qualifications 136 that the healthcare practitioner 106(1) is requesting to be exempted from. The credentialing and privileging module 104(2) may send the exemption request 194 to the reviewer 106(2) or the administrator 106(3). The reviewer 106(2) may review the exemption request 194 and make an exemption recommendation 196 to grant or deny the exemption request 194. The credentialing and privileging module 104(2) may receive the exemption recommendation 196 to grant or deny the exemption request 194 from the reviewer 106(2). The credentialing and privileging module 104(2) may then send the exemption request 194 and the exemption recommendation 196 to the administrator 106(3). The credentialing and privileging module 104(2) may then receive a privilege grant 198 of the exemption request 194 or privilege denial 200 of the exemption request 194 from the administrator 106(3).

In some embodiments, the credentialing and privileging module 104(2) may provide ongoing oversight of the healthcare practitioner 106(1) to ensure that the healthcare practitioner 106(1) is not providing healthcare services that the healthcare practitioner 106(1) is not privileged to provide. For example, in embodiments where the at least one memory 114 stores practitioner data 120 including current privilege data 120(14) and clinical activity data 122 including information on the type of healthcare services provided by the healthcare practitioner 106(1), the credentialing and privileging module 104(2) may determine if the healthcare practitioner 106(1) has provided healthcare services that the healthcare practitioner 106(1) is not privileged to perform at a given facility 134.

The credentialing and privileging module 104(2) may determine if the healthcare practitioner 106(1) has provided healthcare services that the healthcare practitioner 106(1) is not privileged to perform by comparing the practitioner data 120 and the clinical activity data 122. In some embodiments, the credentialing and privileging module 104(2) may determine if the healthcare practitioner 106(1) has provided healthcare services that the healthcare practitioner 106(1) is not privileged to perform by comparing medical codes 156 associated with the healthcare privileges 128(1)-(n) granted to the healthcare practitioner 106(1) in the practitioner data 120 and medical codes 156 associated with the type of healthcare services provided by the healthcare practitioner 106(1) in the clinical activity data 122. The credentialing and privileging module 104(2) may send a notification 180 to one or more users 106(1)-(3) if the healthcare practitioner 106(1) has provided healthcare services that the healthcare practitioner 106(1) is not privileged to provide.

In some embodiments, the credentialing and privileging module 104(2) may provide ongoing oversight of the healthcare practitioner 106(1) to ensure that the healthcare practitioner 106(1) is satisfying the privilege conditions 140 required to maintain the healthcare privileges 128(1)-(n) granted to the healthcare practitioner 106(1). For example, in embodiments where the at least one memory 114 stores practitioner data 120 including information on the conditions required to maintain healthcare privileges 128(1)-(n) granted to the healthcare practitioner 106(1) and clinical activity data 122 including volume data 122(1) and type data 122(2) of healthcare services provided by the healthcare practitioner 106(1), the credentialing and privileging module 104(2) may determine if the healthcare practitioner 106(1) is satisfying the conditions required to maintain the healthcare privileges 128(1)-(n) granted to the healthcare practitioner 106(1).

The credentialing and privileging module 104(2) may determine if the healthcare practitioner 106(1) is satisfying the privilege conditions 140 required to maintain the privileges 128(1)-(n) granted to the healthcare practitioner 106(1) by comparing the practitioner data 120 and the clinical activity data 122. For example, the credentialing and privileging module 104(2) may determine if the healthcare practitioner 106(1) is meeting minimum volume conditions 138(3) for maintaining the privileges 128(1)-(n). In some embodiments, the credentialing and privileging module 104(2) may determine if the healthcare practitioner 106(1) is satisfying the privilege conditions 140 required to maintain the privileges 128(1)-(n) granted to the healthcare practitioner 106(1) by comparing medical codes 156 associated with the privileges 128(1)-(n) granted to the healthcare practitioner 106(1) in the practitioner data 120 and medical codes 156 associated with the healthcare services performed by the healthcare practitioner 106(1) in the clinical activity data 122. The credentialing and privileging module 104(2) may send a notification 180 to one or more users 106(1)-(3) if the conditions for maintaining the granted privileges 128(1)-(n) have not been satisfied.

In some embodiments, the privilege conditions 140 may include evaluating of the healthcare practitioner 106(1) or healthcare services provided by the healthcare practitioner 106(1). The credentialing and privileging module 104(2) may facilitate the evaluation of healthcare practitioners. The credentialing and privileging module 104(2) may generate a privilege condition record 201 for each privilege condition 140 that is required for a healthcare practitioner 106(1) to be granted a healthcare privilege 128 at one or more facilities 134(1)-(n). The privilege conditions record 201 may include information about what the privilege conditions 140 require, the completion deadline, the completion status, and other relevant information. The credentialing and privileging module 104(2) may store evaluation forms 202. The credentialing and privileging module 104(2) may send one of the evaluation forms 202 to a reviewer 106(2) to complete after evaluating the healthcare practitioner 106(1) or healthcare services provided by the healthcare practitioner 106(1). The credentialing and privileging module 104(2) may receive the completed evaluation form 202 from the reviewer 106(2) and may associate the completed evaluation form 202 the privilege condition record 201.

The credentialing and privileging module 104(2) may update the plurality of privilege forms 126(1)-(n) or the healthcare privilege data 118. The credentialing and privileging module 104(2) may receive updates 203 to the plurality of privilege forms 126(1)-(n) or the healthcare privilege data 118 from the administrator 106(3) and/or through an application programming interface. In some embodiments, the updates 203 to the plurality of privilege forms 126(1)-(n) or the healthcare privilege data 118 may be necessary because a healthcare organization may desire to update the healthcare privilege data 118 or the plurality of privilege forms 126(1)-(n) to modify the required qualifications 136 or privilege conditions 138 required for a healthcare practitioner 106(1) to be granted one or more healthcare privileges 128(1)-(n) based on decisions by the healthcare organization or its board members, administrators, or other decisions makers. In other embodiments, the updates 203 to the plurality of privilege forms 126(1)-(n) or the healthcare privilege data 118 may be necessary based on one or more of a federal law, a federal regulation, a state law, a state regulation, or changes thereto. The one or more users 106(1)-(3) may be able to opt out of updates.

In some embodiments, the privilege form 126 sent to the healthcare practitioner 106(1) remains substantially unchanged when the healthcare privilege data 118 or the plurality of privilege forms 126(1)-(n) are updated. In other embodiments, the privilege form 126 sent to the healthcare practitioner 106(1) may be updated based on the updates 203 to the plurality of privilege forms 126(1)-(n) or the healthcare privilege data 118. When the plurality of privilege forms 126(1)-(n) include one or more medical codes 156, the updating the plurality of privilege forms 126(1)-(n) may include modifying the one or more medical codes 156 associated with one or more of the plurality of privilege forms 126(1)-(n).

In some embodiments, system 100 may include a web portal 204. The web portal 204 may be accessible by one or more users 106(1)-(3) through the data network 112 via a user device 110. The steps of receiving or sending form requests 174, privilege forms 126(1)-(n), notifications 180, documentation requests 182, information requests 184, privilege recommendation 186, privilege denial 190, privilege grant 192, exemption 194, exemption recommendations 196, exemption grants 198, exemption denials 200, updates 203 or other data, documents, or information may be performed via the web portal 204.

Insights

In one embodiment, the server 102 may include the insights module 104(3). The insights module 104(3) may be configured to provide analysis and recommendations to improve the credentialing and privileging of healthcare practitioners 106(1). For example, the insights module 104(3) may include non-transitory computer-executable instructions 116 that, when executed by the at least one processor 158, cause the insights module 104(3) to carry out, perform, or implement, one or more steps, actions, operations, or the like. Although such steps, actions, or operations may be described as being performed or implemented by the insights module 104(3), it is understood that such operations may be described as being performed or implemented by the at least one processor 158, the server 102, or the system 100.

The insights module 104(3) may analyze one or more of healthcare privilege data 118, practitioner data 120, clinical activity data 122, and training data 124 received from the healthcare practitioner 106(1) using the neural network 188. The healthcare privilege data 118, practitioner data 120, and clinical activity data 122 may be aggregated and deidentified. In some embodiments, the insights module 104(3) may analyze healthcare privilege data 118 including information on required qualifications 136 for a healthcare practitioner 106(1) to perform each of a plurality of healthcare privileges 128(1)-(n) at a plurality of facilities 134(1)-(n); practitioner data 120 including education data 120(4), training data 124, and certification data 120(8) for the plurality of healthcare practitioners 106(1) and data on the privileges 128(1)-(n) granted to a plurality of healthcare practitioners 106(1) privileged at the plurality of facilities 134(1)-(n); and clinical activity data 122 including volume data 122(1), type data 122(2), and outcome data 122(3) on healthcare services provided by the plurality of healthcare practitioners 106(1).

The insights module 104(3) may generate a required qualifications recommendation 206 to modify the required qualifications 136 for one or more of the plurality of facilities 134(1)-(n) based on the analyzing of the healthcare privilege data 118, practitioner data 120, and clinical activity data 122. The insights module 104(3) may send the required qualifications recommendation 206 to a reviewer 106(2) or administrator 106(3) via the data network 112.

Figure 10:
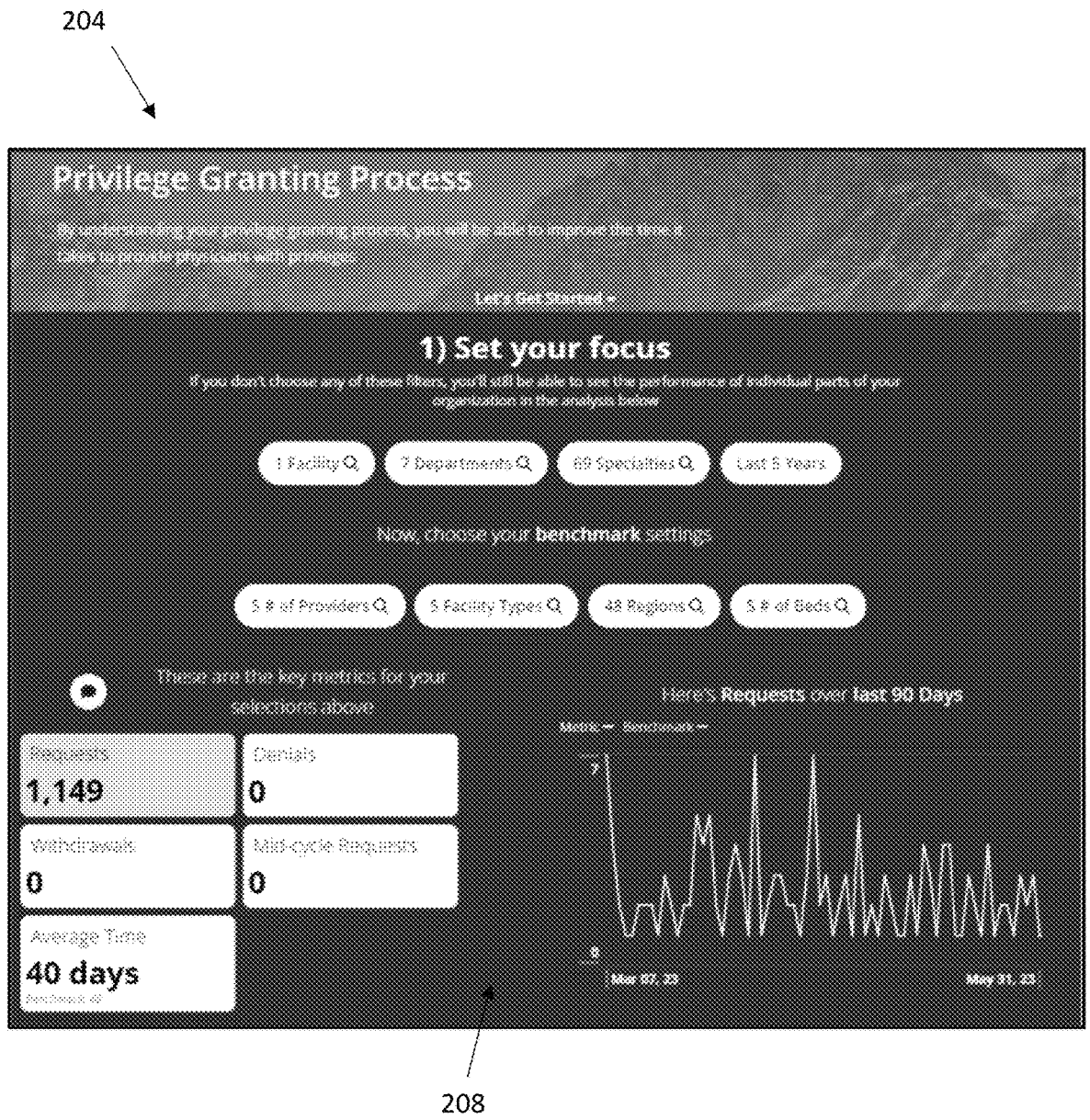
FIG. 10 is a flowchart diagram illustrating another exemplary embodiment of a method for health education, certification, and recordation.

The insights module 104(3) may compare the outcome data 122(3) for healthcare services provided by a first healthcare practitioner 106(1) from the plurality of healthcare practitioners 106(1) to outcome data 122(3) for healthcare services provided by the plurality of healthcare practitioners 106(1). For example, the insights module 104(3) may compare outcome data 122(3) for healthcare services provided by the first healthcare practitioner 106(1) for the plurality of healthcare practitioners 106(1) to the outcome data 122(3) for healthcare services provided by the plurality of healthcare practitioners 106(1) to determine if the outcomes of healthcare services provided by the first healthcare practitioner 106(1) are better or worse than the outcomes of healthcare services provided by the plurality of healthcare practitioners 106(1). The insights module 104(3) may generate an insights report 208, as shown in FIG. 10, based on the comparing of the outcome data 122(3) for healthcare services provided by the first healthcare practitioner 106(1) to the outcome data 122(3) for healthcare services provided by the plurality of healthcare practitioners 106(1). The insights module 104(3) may send the insights report 208 to the first healthcare practitioner 106(1) via the data network 112.

In some embodiments, the at least one memory 114 further stores training data 124 including available training data 124(2). The insights module 104(3) may generate a training recommendation 210 including one or more of the available trainings based on the comparing of the outcome data 122(3) for healthcare services provided by the first healthcare practitioner 106(1) to the outcome data 122(3) for healthcare services provided by the plurality of healthcare practitioners 106(1). For example, the training recommendation 210 may include one or more available trainings related to healthcare services for which the outcomes of the healthcare services when provided by first healthcare practitioner 106(1) are worse than the outcomes of the healthcare services when provided by the plurality of healthcare practitioners 106(1). The insights module 104(3) may send the training recommendation 210 to the first healthcare practitioner 106(1) via the data network 112.

In some embodiments, the healthcare privilege data 118 may include privileging and credentialing outcome data 212 for a plurality of healthcare practitioners 106(1) in a plurality of facilities 134(1)-(n) across a plurality of healthcare organizations 130. The privileging and credentialing outcome data 212 may include data on the turn-around time, risk factors, key delays, volumes, and other relevant data about the credentialing and privileging process and may be on a healthcare practitioner 106(1) or healthcare organization 130 level. The insights module 104(3) may compare the privileging and credentialing outcome data 212 for the plurality of healthcare practitioners 106(1) in each of the healthcare organizations 130 to the privileging and credentialing outcome data for the plurality of healthcare practitioners 106(1) in at least one other of the plurality of healthcare organizations 130. The insights module 104(3) may determine if the privileging and credentialing outcomes at one of the plurality of healthcare organizations 130 is better than the privileging and credentialing outcomes at other of the plurality of healthcare organizations 130. For example, the insights module 104(3) may determine if a healthcare organization 130 is performing better or worse than other healthcare organizations 130 on a particular aspect of credentialing and privileging (turn-around time, risk factors, key delays, volumes, etc.). The insight module 104(3) may then generate a recommendation of how to improve the credentialing and privileging process at the healthcare organization 130, such as by changing the credentialing and privileging procedure.

Computer-Implemented Methods

Figure 11:
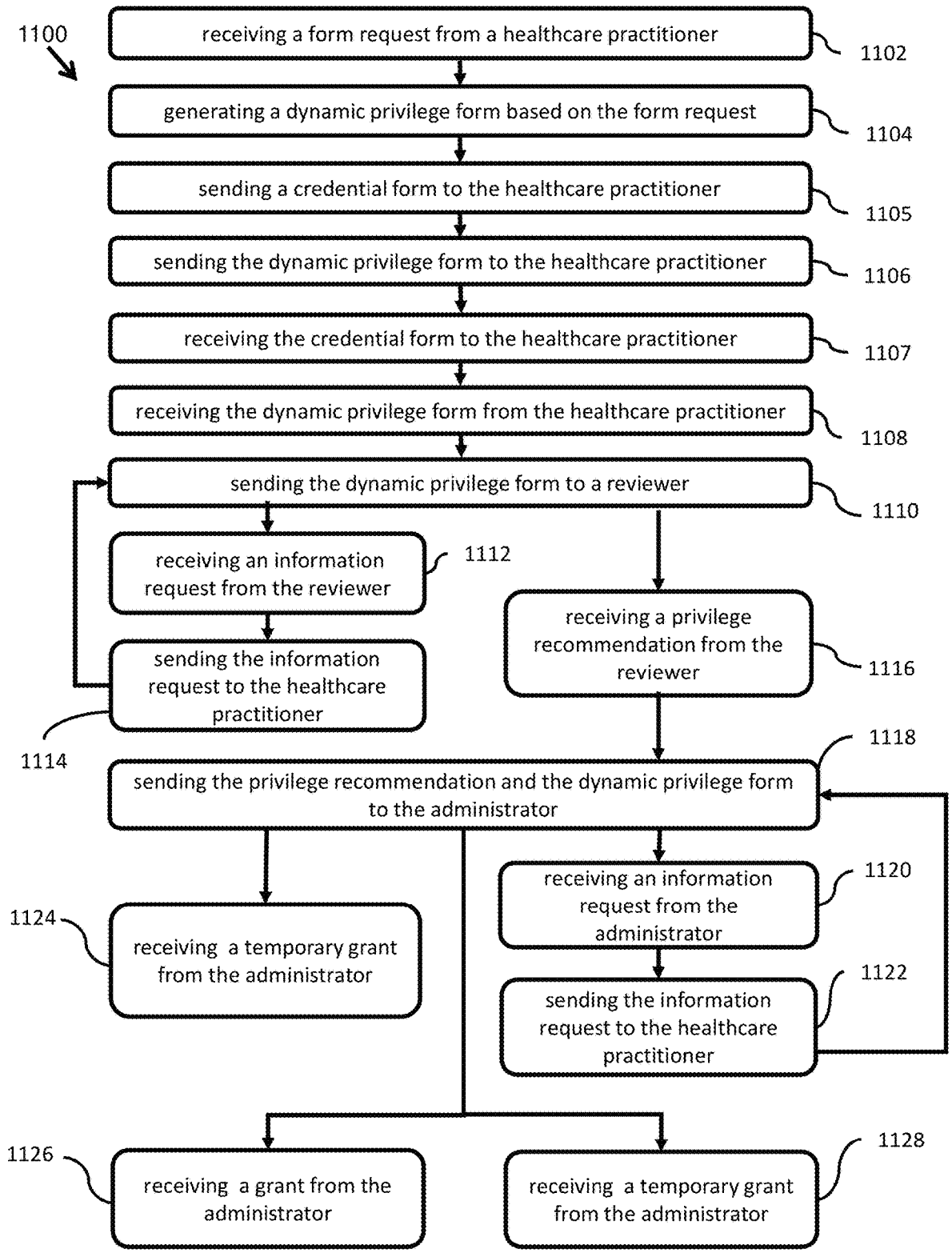
FIG. 11 is a flowchart diagram illustrating another exemplary embodiment of a method for health education, certification, and recordation.
Figure 12:
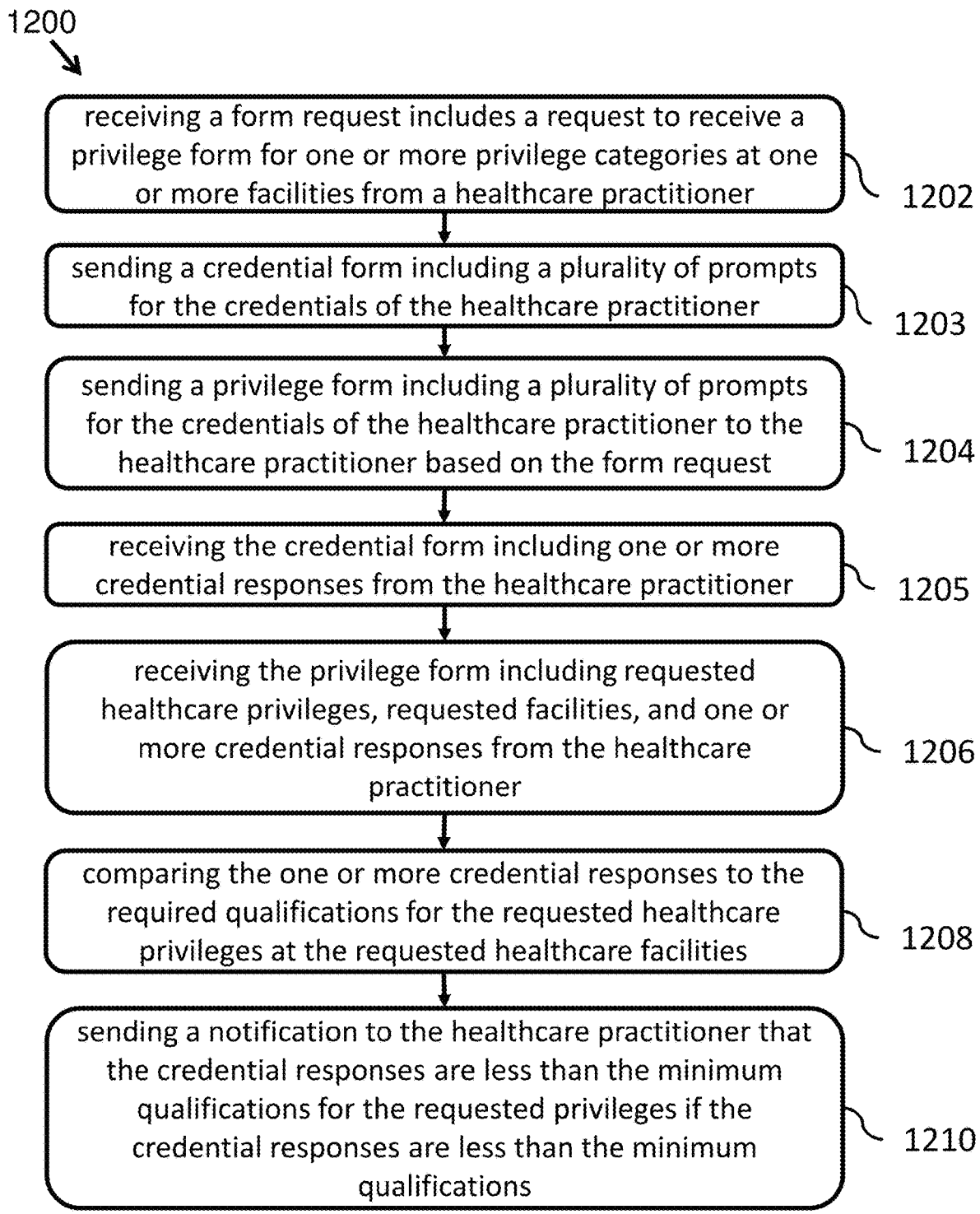
FIG. 12 is a flowchart diagram illustrating another exemplary embodiment of a method for health education, certification, and recordation.
Figure 13:
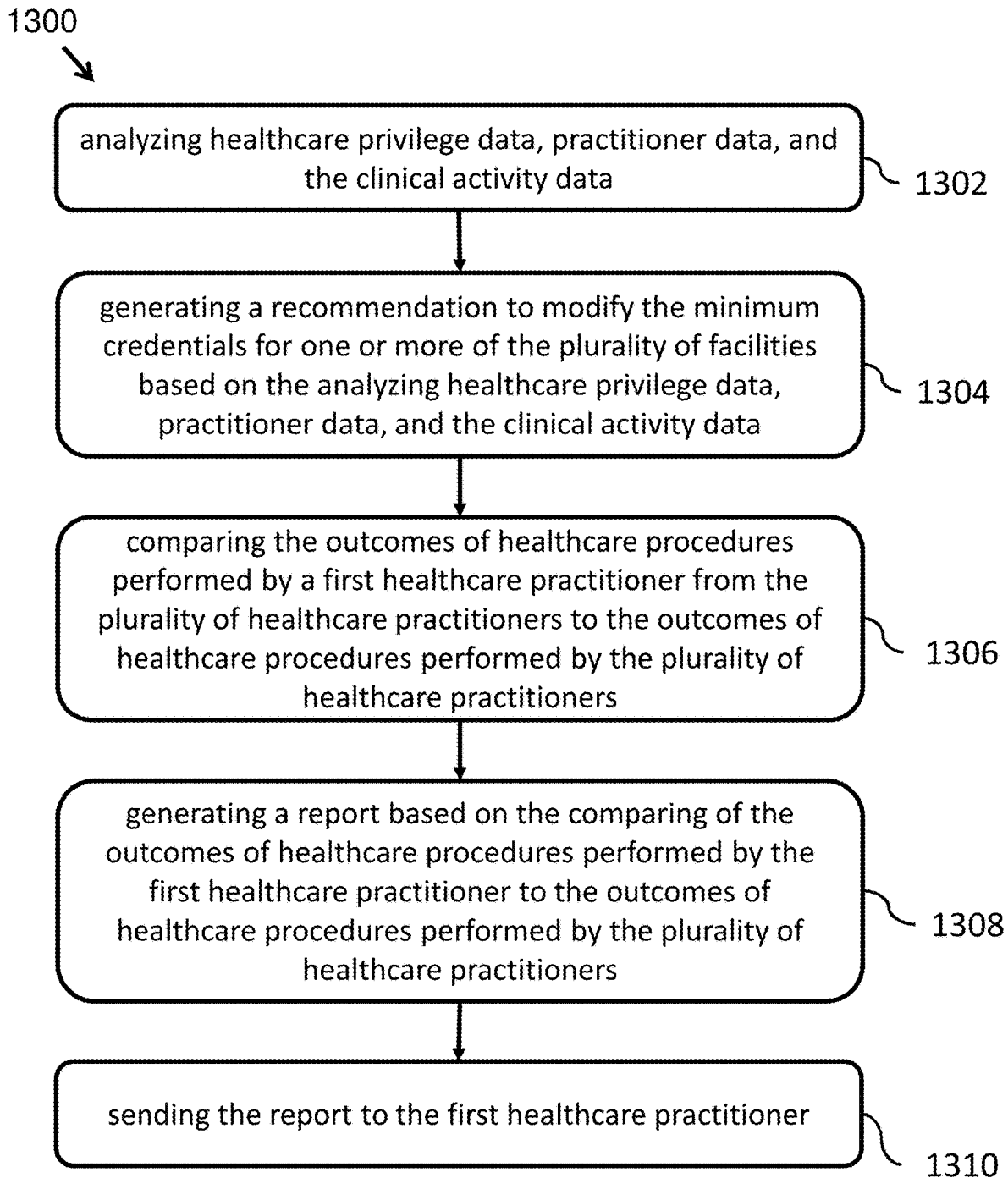
FIG. 13 is a flowchart diagram illustrating another exemplary embodiment of a method for education, certification, and recordation.

FIGS. 11-13 depict various embodiments of methods of the present disclosure. The methods may be computer-implemented methods. The methods may include one or more steps. Some embodiments of the methods may include providing a system 100. The system 100 may include the system 100 of FIG. 1 or other systems 100 described herein. The system 100 may include the server 102 with at least one processor 158 and at least one memory 114. In some embodiments, the methods may include storing one or more non-transitory computer-executable instructions 116 and/or a plurality of privilege forms 126(1)-(n). The methods may include executing the non-transitory computer-executable instructions 116 on the at least one processor 158.

In the embodiment shown in FIG. 11, the method 1100 may include receiving 1102 a form request 174 from a healthcare practitioner 106(1). The request form 174 may include a request to receive a dynamic privilege form 126 for one or more privilege categories 140 at one or more facilities 134(1)-(n). The method 1100 may include generating 1104 a dynamic privilege form 126 based on the form request 174. The dynamic privilege form 126 may include one or more healthcare privileges 128(1)-(n) and one or more facilities 134(1)-(n) for selection by the healthcare practitioner 106(1). In some embodiments, the step of generating the dynamic privilege form 126 includes generating the dynamic privilege form 126 based on one or more of the plurality of privilege forms 126(1)-(n).

The method 1100 may include sending 1105 to the healthcare practitioner 106(1) a credential form 175 including a plurality of prompts 176 for the credentials of the healthcare practitioner 106(1). The method 1100 may include sending 1106 the dynamic privilege form 126 to the healthcare practitioner 106(1). The method 1107 may also include receiving the credential form 175 including one or more credential responses 178 to the plurality of prompts 176 from the healthcare practitioner 106(1). The method 1100 may also include receiving 1108 the dynamic privilege form 126 from the healthcare practitioner 106(1). The dynamic privilege form 126 received 1108 may include requested healthcare privileges 129 from the one or more healthcare privileges 128(1)-(n) and requested facilities 135 from the one or more facilities 134(1)-(n). The method 1100 may include sending 1110 the credential form 175 with the one or more credential responses 178 and the dynamic privilege form 126 with the requested healthcare privileges 129 and the requested facilities 135 to a reviewer 106(2). In some embodiments, the method 1100 may include receiving 1112 an information request 184 from the reviewer. In such embodiments, the method 1100 may include sending 1114 the information request 184, the credential form 175 with the one or more credential responses 178, and the privilege form 126 with the requested healthcare privileges 129, the requested facilities 135, and the one or more credential responses 178 to the healthcare practitioner 106(1). In other embodiments, the method may include receiving 1116 a privilege recommendation 186 to either grant or deny one or more of the requested healthcare privileges 129 at one or more of the requested facilities 135 from the reviewer 106(2). In such embodiments, the method 1100 may include sending 1118 the privilege recommendation 186, the credential form 175 with the one or more credential responses 178, and the dynamic privilege form 126 with the requested healthcare privileges 129 and the requested facilities 135 to the administrator 106(3).

In some embodiments, the method 1100 may include receiving 1120 an information request 184 from the administrator 106(3) and sending 1122 the information request 184, the credential form 175 with the one or more credential responses 178, and the dynamic privilege form 126 with the requested healthcare privileges 129 and the requested facilities 135 to the healthcare practitioner 106(1). The method 1100 may also include receiving 1124 a temporary privilege grant 191 of one or more of the requested healthcare privileges 129 at one or more of the requested facilities 135 from the administrator 106(3), receiving 1126 a grant of one or more of the requested healthcare privileges 129 at one or more of the requested healthcare facilities 134 from the administrator 106(3), and/or receiving 1128 a denial of one or more of the requested healthcare privileges 129 at one or more of the requested healthcare facilities 134 from the administrator 106(3).

In the embodiment shown in FIG. 12, the method 1200 may include receiving 1202 a form request 174 including a request to receive a privilege form 126 for one or more privilege categories 140 at one or more facilities 134 from a healthcare practitioner 106(1). The method may include 1203 sending a credential form 175 including a plurality of prompts 176 for the credentials of the healthcare practitioner 106(1). The method 1200 may also include sending 1204 a privilege form 126 including requested healthcare privileges 129 from the one or more healthcare privileges 128(1)-(n) and requested facilities 134 from the one or more facilities 134(1)-(n) based on the form request 174. The method may include 1205 receiving the credential form 175 including one or more credential responses 178 from the healthcare practitioner 106(1). The method 1200 may include receiving 1206 the privilege form 126 including requested healthcare privileges 129 and requested facilities 135, from the healthcare practitioner 106(1). The method 1200 may include comparing 1208 the one or more credential responses 178 to the required qualifications 136 for the requested healthcare privileges 129 at the requested healthcare facilities 134. The method 1200 may include sending 1210 a notification 180 to the healthcare practitioner 106(1) that the credential responses 178 are less than the required qualifications 136 for the requested privileges 128 if the credential responses 178 are less than the required qualifications 136.

In the embodiment shown in FIG. 13, the method 1300 may include analyzing 1302 healthcare privilege data 118, practitioner data 120, and the clinical activity data 122. The method may include generating 1304 a required qualifications recommendation 206 to modify the required qualifications 136 for one or more of the plurality of facilities 134(1)-(n) based on the analyzing healthcare privilege data 118, practitioner data 120, and the clinical activity data 122. The method 1300 may include comparing 1306 outcome data 122(3) for healthcare services performed by a first healthcare practitioner 106(1) from the plurality of healthcare practitioners 106(1) to the outcome data 122(3) of healthcare services provided by the plurality of healthcare practitioners 106(1). The method 1300 may include generating 1308 an insights report 208 based on the comparing of the outcome data 122(3) of healthcare services provided by the first healthcare practitioner 106(1) to the outcome data 122(3) of healthcare services provided by the plurality of healthcare practitioners 106(1). The method 1300 may also include sending 1310 the report to the first healthcare practitioner 106(1).

Some of the steps of the above-described methods 1100, 1200, 1300 have been described above. In some embodiments, other elements of the systems 100 may perform one or more of those steps, not just those described in relation to the methods 1100, 1200, 1300. For example, in some embodiments, one or more modules 106(1)-(3) may perform one or more of the steps of the method 1100, 1200, 1300. In one or more embodiments, a step of a method 1100, 1200, 1300 may include sub-steps or functionality described above in relation to FIGS. 1-10, although not explicitly described in relation to FIGS. 11-13.

Misc

In some embodiments, a user of the system 100 may include a person that works at healthcare facility but does not access the system 100 himself or herself but has another person (such as hospital support staff) access the system 100 on the user's behalf. For example, a healthcare provider that works at a hospital may not use a client device 120 to interact with the server 110, however a hospital support staff may use a client device 120 to update the healthcare provider's user account information, track the healthcare provider's progress in credentialing and privileging, or perform other system 100 functionality.

In some embodiments, a module (such as the account module 104(1), credentialing and privileging module 104(2), the insight module 104(3), or other module 104) storing data may include the module storing the data in an area of a file system of the server 110 that the module controls. In other embodiments, the module storing data may include the module storing data in a database. The database may be a database stored on the server 110 or may include a database on another device.

In some embodiments, one or more modules of the server 110 may send data to an external data repository. The external data repository may include a PSO. Before the server 110 sends the data to the PSO, the server 110 may strip the data of identifying information or other information such that the data complies with healthcare information regulation (e.g., the Health Insurance Portability and Accountability Act (HIPAA)). In some embodiments, the data sent to the PSO may include a healthcare protocol used on a patient in an actual medical episode, the outcome of using the healthcare protocol, or other data. The PSO may use the received data to improve healthcare protocols, training, or other information. The PSO may send updated healthcare protocol data to the server 110.

Computer Hardware and Software

As will be appreciated by one skilled in the art, aspects of the present disclosure may be embodied as an apparatus, system, method, computer program product, or the like. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module," or "system." Furthermore, aspects of the present disclosure may take the form of a computer program product embodied in one or more computer readable medium(s) having program code embodied thereon.

In some embodiments, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of program code may, for instance, comprise one or more physical or logical blocks of computer instructions which may, for instance, be organized as an object, procedure, or function. Nevertheless, the executables of an identified module need not be physically located together but may comprise disparate instructions stored in different locations which, when joined logically together, comprise the module and achieve the stated purpose for the module.

Indeed, a module of program code may be a single instruction, or many instructions, and may even be distributed over several different code segments, among different programs, and across several memory devices. Similarly, operational data may be identified and illustrated herein within modules and may be embodied in any suitable form and organized within any suitable type of data structure. The operational data may be collected as a single data set or may be distributed over different locations including over different storage devices, and may exist, at least partially, merely as electronic signals on a system or network. Where a module or portions of a module are implemented in software, the program code may be stored and/or propagated on in one or more computer readable medium(s).

The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processor devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processor device receives computer readable program instructions from the network and forwards the computer readable program instructions for storage in a computer readable storage medium within the respective computing/processor device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the C programming language or similar programming languages. The computer readable program instructions may execute on a supercomputer, a compute cluster, or the like. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations or block diagrams of methods, apparatuses, systems, or computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The schematic flow chart diagrams included herein are generally set forth as logical flow chart diagrams. As such, the depicted order and labeled steps are indicative of one embodiment of the presented method. Other steps and methods may be conceived that may be equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The schematic flowchart diagrams and/or schematic block diagrams in the Figures illustrate the architecture, functionality, and operation of possible implementations of apparatuses, systems, methods and computer program products according to various embodiments of the present disclosure. In this regard, each block in the schematic flowchart diagrams and/or schematic block diagrams may represent a module, segment, or portion of code, which comprises one or more executable instructions of the program code for implementing the specified logical function(s).

It should also be noted that, in some alternative implementations, the functions noted in the block may occur out of the order noted in the Figures. For example, two blocks shown in succession may, in fact, be executed concurrently, or the blocks may sometimes be executed in the reverse order, depending upon the functionality involved. Other steps and methods may be conceived that are equivalent in function, logic, or effect to one or more blocks, or portions thereof, of the illustrated Figures.

Although various arrow types and line types may be employed in the flowchart and/or block diagrams, they are understood not to limit the scope of the corresponding embodiments. Indeed, some arrows or other connectors may be used to indicate only the logical flow of the depicted embodiment. For instance, an arrow may indicate a waiting or monitoring period of unspecified duration between enumerated steps of the depicted embodiment. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and program code.

Other embodiments of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A system for credentialing and privileging of a healthcare practitioner, comprising:
    a server comprising at least one computing device, at least one module, at least one memory, and at least one input/output (I/O) interface;
    at least one client device;
    at least one processor, wherein the server, the at least one client device, and the at least one processor are configured for at least one of wired or wireless communication over a data network; and
    wherein the at least one memory is configured to store one or more non-transitory computer-executable instructions,
    wherein the at least one processor, in response to executing the one or more non-transitory computer-executable instructions, implements a method comprising:
        receiving a form request from a healthcare practitioner, wherein the form request includes a request to receive a dynamic privilege form in one or more privilege categories for one or more facilities;
        generating the dynamic privilege form based on the form request, the dynamic privilege form including one or more healthcare privileges and one or more facilities for selection by the healthcare practitioner;
        sending a credential form including a plurality of prompts for the credentials of the healthcare practitioner;
        sending the dynamic privilege form to the healthcare practitioner;
        receiving the credential form including one or more credential responses to the plurality of prompts from the healthcare practitioner; and
        receiving the dynamic privilege form from the healthcare practitioner, the dynamic privilege form including requested healthcare privileges from the one or more healthcare privileges and requested facilities from the one or more facilities; and
        wherein the at least one memory stores a plurality of privilege forms for the one or more privilege categories, and wherein the step of generating the dynamic privilege form includes generating the dynamic privilege form that is customizable based on modification of at least one of the plurality of privilege forms.

2. The system of claim 1, wherein the one or more privilege categories, include at least one of
    a specialty category,
    a care setting category,
    a practitioner category, and
    a procedure category.

3. The system of claim 1, wherein the dynamic privilege form includes one or more medical codes associated with the one or more healthcare privileges.

4. The system of claim 3, wherein the one or more medical codes include ICD-10 codes, CPT codes, or both.

5. The system of claim 1, wherein the method implemented by the at least one processor further comprises updating the plurality of privilege forms.

6. The system of claim 5, wherein the updating of the plurality of privilege forms is based on a change made to one or more of a federal law, a federal regulation, a state law, and a state regulation.

7. The method of claim 5, wherein the dynamic privilege form is substantially unchanged after the updating of the plurality of privilege forms.

8. The method of claim 5, wherein the method implemented by the at least one processor further comprises updating the dynamic privilege form based on the updating of the plurality of privilege forms.

9. The system of claim 5, wherein updating of the plurality of privilege forms is performed via an application programming interface.

10. The system of claim 5, wherein the plurality of privilege forms are each associated with one or more medical codes, and wherein the updating of the plurality of privilege forms includes modifying the one or more medical codes associated with one or more of the plurality of privilege forms.

11. The system of claim 1, wherein the method implemented by the at least one processor further comprises:
sending the credential form with the one or more credential responses and the dynamic privilege form with the requested healthcare privileges and the requested facilities to a reviewer;
receiving an information request from the reviewer; and
sending the information request, the credential form with the one or more credential responses, and the dynamic privilege form with the requested healthcare privileges and the requested facilities to the healthcare practitioner.

12. The system of claim 1, wherein the method implemented by the at least one processor further comprises:
sending the credential form with the one or more credential responses and the dynamic privilege form with the requested healthcare privileges and the requested facilities to a reviewer;
receiving a privilege recommendation to either grant or deny one or more of the requested healthcare privileges at one or more of the requested facilities from the reviewer; and
sending the privilege recommendation, the credential form with the one or more credential responses, and the dynamic privilege form with the requested healthcare privileges and the requested facilities to an administrator.

13. The system of claim 12, wherein the method implemented by the at least one processor further comprises:
receiving an information request from the administrator; and
sending the information request, the credential form with the one or more credential responses, and the dynamic privilege form with the requested healthcare privileges and the requested facilities to the healthcare practitioner.

14. The system of claim 13, wherein the method implemented by the at least one processor further comprises receiving a temporary privilege grant for one or more of the requested healthcare privileges at one or more of the requested facilities from the administrator.

15. The system of claim 12, wherein the method implemented by the at least one processor further comprises receiving a privilege grant for one or more of the requested healthcare privileges at one or more of the requested healthcare facilities from the administrator.

16. The system of claim 12, wherein the method implemented by the at least one processor further comprises receiving a privilege denial for one or more of the requested healthcare privileges at one or more of the requested healthcare facilities from the administrator.

17. The system of claim 1, wherein the at least one memory further stores healthcare privilege data including the one or more healthcare privileges, wherein the one or more healthcare privileges are organized into privilege groups including at least two of the one or more healthcare privileges, and wherein the dynamic privilege form includes one or more privilege groups.

18. The system of claim 17, wherein the at least two of the one or more healthcare privileges in each privilege group have the same required qualifications to be granted to the healthcare practitioner at the one or more facilities of the dynamic privilege form.

19. The system of claim 17, wherein the method implemented by the at least one processor includes receiving updates to the healthcare privilege data from the administrator.

20. The system of claim 17, wherein the at least one memory further stores source documentation for each privilege group, and wherein the method implemented by the at least one processor further comprises:
receiving a request for the source documentation from the healthcare practitioner, and sending the source documentation to the healthcare practitioner.

21. The system of claim 1, wherein the at least one memory further stores practitioner data for the healthcare practitioner, the practitioner data including educations data, training data, and certification data for the healthcare practitioner, and the method implemented by the at least one processor further comprises generating one or more credential responses to the plurality of prompts in the credential form based on the practitioner data.

22. The system of claim 1, wherein the at least one memory further stores clinical activity data for the healthcare practitioner, the clinical activity data including volume data and type data for healthcare services provided by the healthcare practitioner, and wherein the method implemented by the at least one processor further comprises generating one or more credential responses to the plurality of prompts in the credential form based on the clinical activity data.

23. The system of claim 1, wherein the at least one memory stores privilege conditions required to maintain privileges granted to the healthcare practitioner, wherein the at least one memory stores clinical activity data including volume data and type data for healthcare services provided by the healthcare practitioner, and wherein the method implemented by the at least one processor further comprises:
determining if the conditions for maintaining the granted privileges have been satisfied by comparing the privilege conditions and the clinical activity data; and
sending a notification to one or more users if the privilege conditions for maintaining the granted privileges have not been satisfied.

24. The system of claim 23, wherein the method implemented by the at least one processor further comprises revoking one or more of the privileges granted to the healthcare practitioner if the privilege conditions for maintaining the granted privileges have not been met.

25. The system of claim 1, wherein the one or more credential responses include one or more of an education response, a training response, a certification response, and a work experience response.

26. The system of claim 1, wherein the form request includes a request to receive the dynamic privilege form for the one or more privilege categories at a single healthcare facility, a plurality of healthcare facilities within a single healthcare system, or a plurality of healthcare facilities across two or more healthcare systems.

27. The system of claim 1, wherein the method implemented by the at least one processor further comprises:
sending the credential form with the one or more credential responses and the dynamic privilege form with the requested healthcare privileges and the requested facilities to an administrator;

receiving a denial of one or more of the requested healthcare privileges at one or more of the requested facilities from the administrator;

sending the credential form with the one or more credential responses and the dynamic privilege form with the requested healthcare privileges and the requested facilities, to the healthcare practitioner;

receiving the credential form with the modifications to the one or more credential responses or the dynamic privilege form with modifications to at least one of the requested healthcare privileges or the requested facilities from the healthcare practitioner; and sending the credential form with the modifications to the one or more credential responses or the dynamic privilege form with the modifications to at least one of the requested healthcare privileges or the requested facilities to the administrator.

28. A system for credentialing and privileging of a healthcare practitioner, comprising:

a server comprising at least one computing device, at least one module, at least one memory, and at least one input/output (I/O) interface;

at least one client device;

at least one processor, wherein the server, the at least one client device, and the at least one processor are configured for at least one of wired or wireless communication over a data network; and wherein the at least one memory is configured to store one or more non-transitory computer-executable instructions, wherein the at least one processor, in response to executing the one or more non-transitory computer-executable instructions, implements a method comprising:

receiving a form request from a healthcare practitioner, wherein the form request includes a request to receive a dynamic privilege form in one or more privilege categories for one or more facilities;

generating the dynamic privilege form based on the form request, the dynamic privilege form including one or more healthcare privileges and one or more facilities for selection by the healthcare practitioner;

sending a credential form including a plurality of prompts for the credentials of the healthcare practitioner;

sending the dynamic privilege form to the healthcare practitioner;

receiving the credential form including one or more credential responses to the plurality of prompts from the healthcare practitioner; and receiving the dynamic privilege form from the healthcare practitioner, the dynamic privilege form including requested healthcare privileges from the one or more healthcare privileges and requested facilities from the one or more facilities;

wherein the at least one memory stores practitioner data including current privilege data for the healthcare practitioner, wherein the at least one memory stores clinical activity data including volume data and type data for healthcare services provided by the healthcare practitioner, and wherein the method implemented by the at least one processor further comprises:

comparing the current privilege data with the volume data and type data;

determining if the healthcare practitioner has provided healthcare services that the healthcare practitioner is not privileged to provide based on the comparing of the current privilege data with the volume data and type data; and sending a notification to one or more users if the healthcare practitioner has provided healthcare services that the healthcare practitioner is not privileged to provide.

29. A system for credentialing and privileging of a healthcare practitioner, comprising:

a server comprising at least one computing device, at least one module, at least one memory, and at least one input/output (I/O) interface;

at least one client device;

at least one processor, wherein the server, the at least one client device, and the at least one processor are configured for at least one of wired or wireless communication over a data network; and wherein the at least one memory is configured to store one or more non-transitory computer-executable instructions, wherein the at least one processor, in response to executing the one or more non-transitory computer-executable instructions, implements a method comprising:

receiving a form request from a healthcare practitioner, wherein the form request includes a request to receive a dynamic privilege form in one or more privilege categories for one or more facilities;

generating the dynamic privilege form based on the form request, the dynamic privilege form including one or more healthcare privileges and one or more facilities for selection by the healthcare practitioner;

sending a credential form including a plurality of prompts for the credentials of the healthcare practitioner;

sending the dynamic privilege form to the healthcare practitioner;

receiving the credential form including one or more credential responses to the plurality of prompts from the healthcare practitioner; and receiving the dynamic privilege form from the healthcare practitioner, the dynamic privilege form including requested healthcare privileges from the one or more healthcare privileges and requested facilities from the one or more facilities;

wherein the at least one memory further stores practitioner data including education data, certification data, and training data for the healthcare practitioner and clinical activity data including volume data and type data for healthcare services provided by the healthcare practitioner, and wherein the method implemented by the at least one processor further comprises:

implementing a neural network configured to make recommendations on whether to grant or deny one or more of the requested healthcare privileges at one or more of the requested facilities;

analyzing the practitioner data, the clinical activity data, the credential form with the modifications to the one or more credential responses, and the dynamic privilege form with the requested healthcare privileges and the requested facilities via the neural network, and sending a recommendation to one or more users to grant or deny one or more of the requested healthcare privileges at one or more of the requested facilities to the healthcare practitioner based on the analyzing of the practitioner data, the clinical activity data, the credential form with the modifications to the one or more credential responses, and the dynamic privilege form with the requested healthcare privileges and the requested facilities via the neural network.

\* \* \* \* \*